US010251736B2

(12) United States Patent
Nakai

(10) Patent No.: US 10,251,736 B2
(45) Date of Patent: Apr. 9, 2019

(54) ROOT CANAL TREATING DEVICE

(71) Applicant: J. MORITA MFG. CORP., Kyoto-shi (JP)

(72) Inventor: Teruji Nakai, Kyoto (JP)

(73) Assignee: J. MORITA MFG. CORP., Kyoto-shi (JP)

( * ) Notice: Subject to any disclaimer, the term of this patent is extended or adjusted under 35 U.S.C. 154(b) by 93 days.

(21) Appl. No.: 15/360,363

(22) Filed: Nov. 23, 2016

(65) Prior Publication Data

US 2017/0071713 A1    Mar. 16, 2017

Related U.S. Application Data

(63) Continuation of application No. PCT/JP2015/065231, filed on May 27, 2015.

(30) Foreign Application Priority Data

May 28, 2014  (JP) .................................. 2014-109866

(51) Int. Cl.
*A61C 19/00* (2006.01)
*A61C 19/04* (2006.01)
(Continued)

(52) U.S. Cl.
CPC .............. *A61C 19/042* (2013.01); *A61B 1/04* (2013.01); *A61B 1/247* (2013.01); *A61B 5/0084* (2013.01);
(Continued)

(58) Field of Classification Search
CPC ..... A61C 19/041; A61C 19/042; A61C 19/04; A61C 1/082; A61C 5/40; A61C 5/42; A61C 5/44
See application file for complete search history.

(56) References Cited

U.S. PATENT DOCUMENTS 7,748,979 B2 * 7/2010 Nahlieli ................. A61B 1/247
433/102
8,129,359 B2 * 3/2012 Herzberg .............. A61L 31/042
514/54
(Continued)

FOREIGN PATENT DOCUMENTS

EP        2 774 543 A1    9/2014
JP        59-036319 U     3/1984
(Continued)

OTHER PUBLICATIONS

International Search Report dated Aug. 18, 2015 in PCT/JP2015/065231, filed May 27, 2015.
(Continued)

*Primary Examiner* — Ralph Lewis
(74) *Attorney, Agent, or Firm* — Oblon, McClelland, Maier & Neustadt, L.L.P.

(57) ABSTRACT

A root canal treatment apparatus includes a root canal treatment hand piece having a visible light camera which captures a visible light image of a tooth as a target of interest, and circuitry which detects a position of the root canal treating hand piece, and instructs display of three images corresponding to at least a tip position of a cutting tool attached to the root canal treating hand piece, an X-ray cross-sectional image of the tooth captured by X-ray CT image capturing beforehand, and the visible light image captured by the visible light camera such that the three images are displayed on a display in an overlapping manner in positional correspondence with one another, based on information on the position of the root canal treating hand piece detected by the circuitry.

16 Claims, 16 Drawing Sheets

(51) Int. Cl.
  *A61B 6/03* (2006.01)
  *A61B 6/14* (2006.01)
  *A61C 5/40* (2017.01)
  *A61B 1/04* (2006.01)
  *A61B 1/247* (2006.01)
  *A61B 5/00* (2006.01)
  *A61B 6/00* (2006.01)
  *A61C 1/08* (2006.01)
  *A61C 5/42* (2017.01)
  *A61C 5/44* (2017.01)
  *A61B 34/20* (2016.01)

(52) U.S. Cl.
  CPC .............. *A61B 5/0088* (2013.01); *A61B 6/03* (2013.01); *A61B 6/032* (2013.01); *A61B 6/14* (2013.01); *A61B 6/463* (2013.01); *A61B 6/5247* (2013.01); *A61C 1/082* (2013.01); *A61C 5/40* (2017.02); *A61C 5/42* (2017.02); *A61C 5/44* (2017.02); *A61C 19/04* (2013.01); *A61C 19/041* (2013.01); *A61B 2034/2055* (2016.02); *A61B 2034/2065* (2016.02)

(56) References Cited

U.S. PATENT DOCUMENTS

| | | | | |
|---|---|---|---|---|
| 8,385,617 | B2* | 2/2013 | Okawa | A61B 1/247 382/128 |
| 2008/0241783 | A1* | 10/2008 | Yamashita | A61C 19/041 433/72 |
| 2011/0229839 | A1* | 9/2011 | Yamashita | A61B 5/053 433/27 |
| 2014/0342301 | A1* | 11/2014 | Fleer | A61C 5/025 433/27 |
| 2017/0071713 | A1* | 3/2017 | Nakai | A61C 19/041 |

FOREIGN PATENT DOCUMENTS

| | | |
|---|---|---|
| JP | 2001-051593 A | 2/2001 |
| JP | 2006-305203 A | 11/2006 |
| JP | 2007-512854 A | 5/2007 |
| JP | 2009-153785 A | 7/2009 |
| JP | 2009-531128 A | 9/2009 |
| JP | 2010-200869 A | 9/2010 |
| JP | 2011-030637 A | 2/2011 |
| JP | 2012-011068 A | 1/2012 |
| JP | 2012-045198 A | 3/2012 |
| JP | 2013-519479 A | 5/2013 |
| JP | 5483518 B2 | 5/2014 |
| JP | 2014-520637 A | 8/2014 |
| JP | 2014-171488 A | 9/2014 |
| JP | 2014-236957 A | 12/2014 |
| WO | WO 2013/010138 A2 | 1/2013 |

OTHER PUBLICATIONS

Office Action dated May 19, 2015 in Japanese Patent Application No. 2014-109866, filed May 28, 2014 (with English-language Translation).

Extended European Search Report dated Dec. 20, 2017 in Patent Application No. 15800555.3, 7 pages.

* cited by examiner

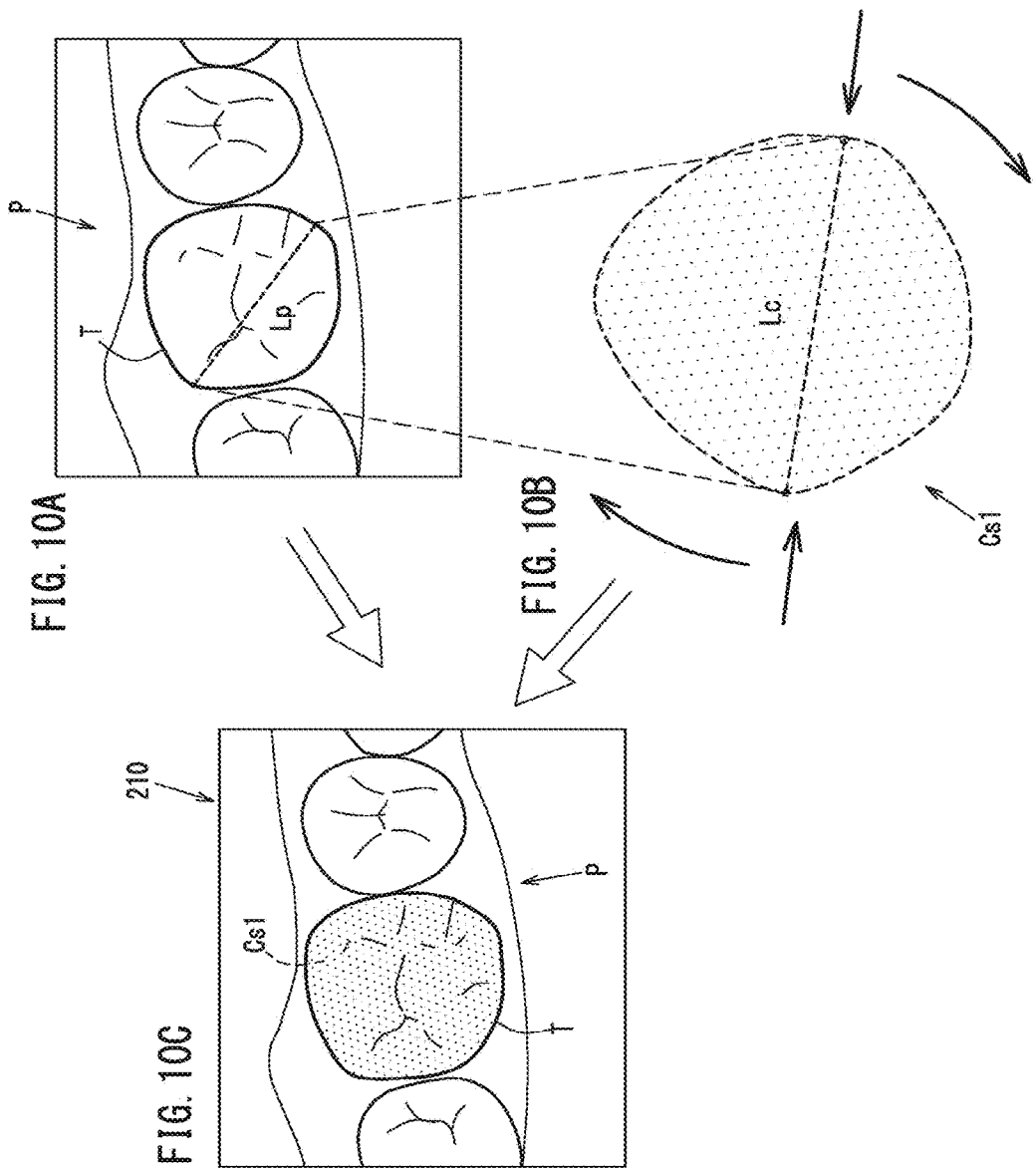

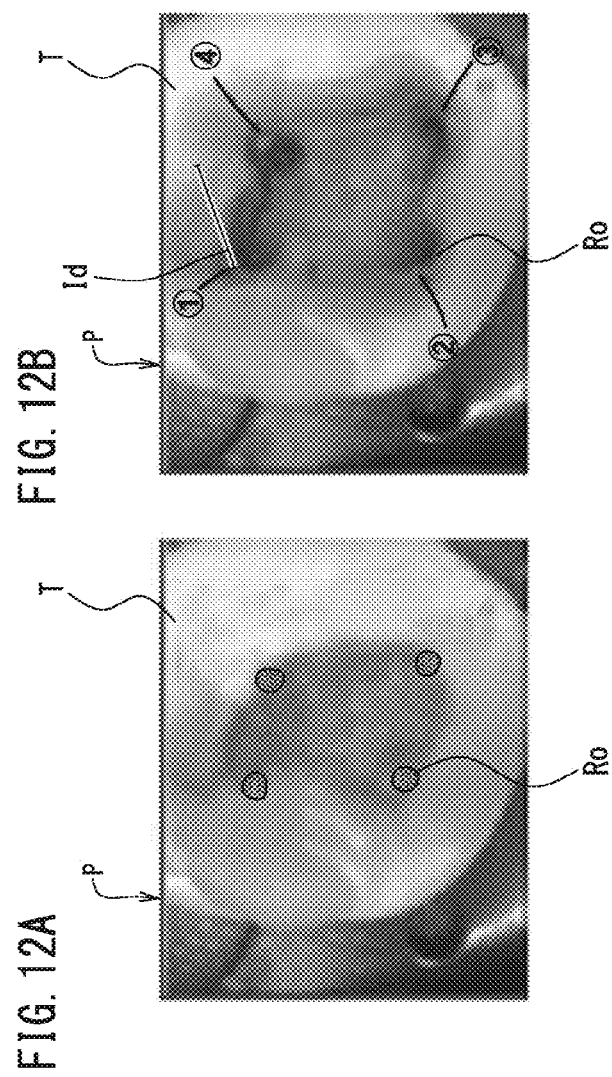

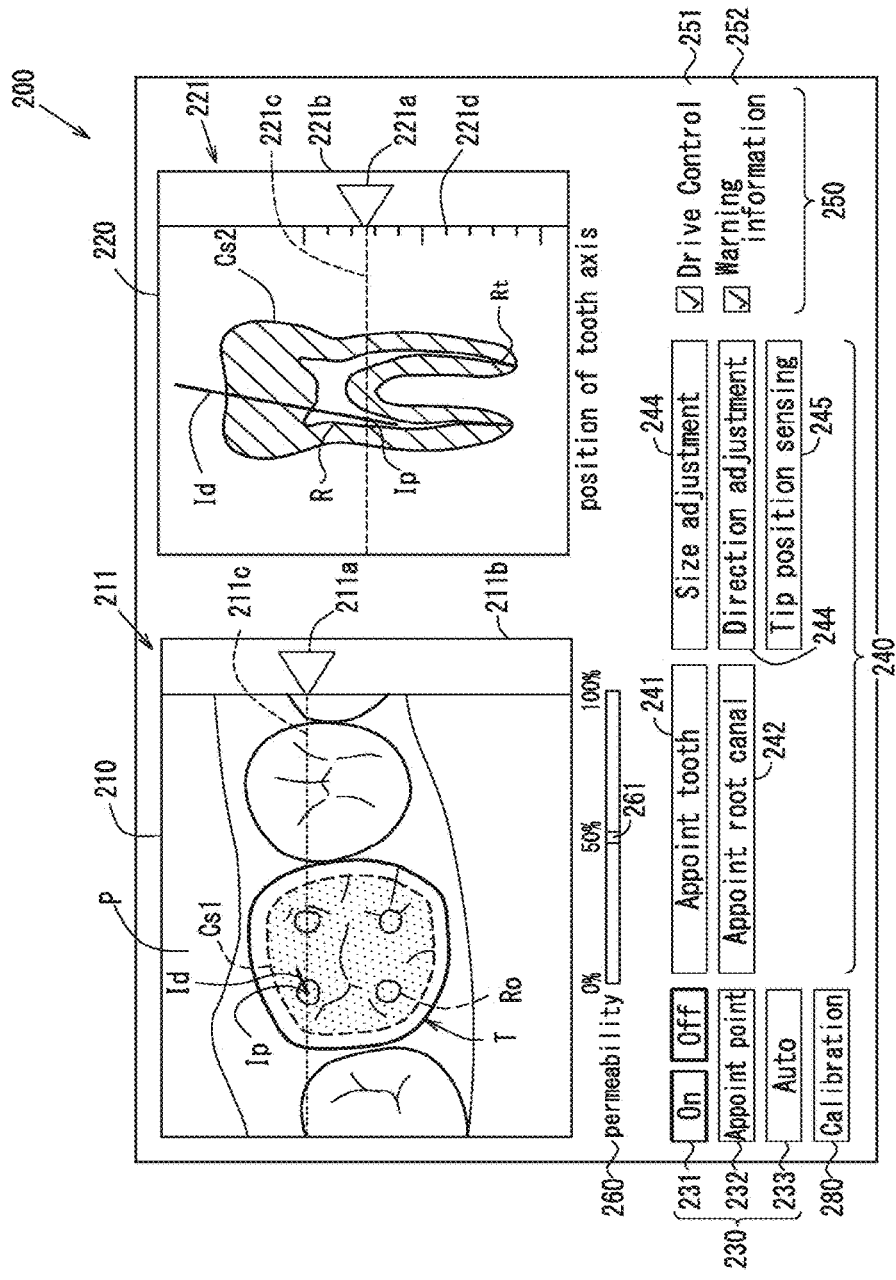

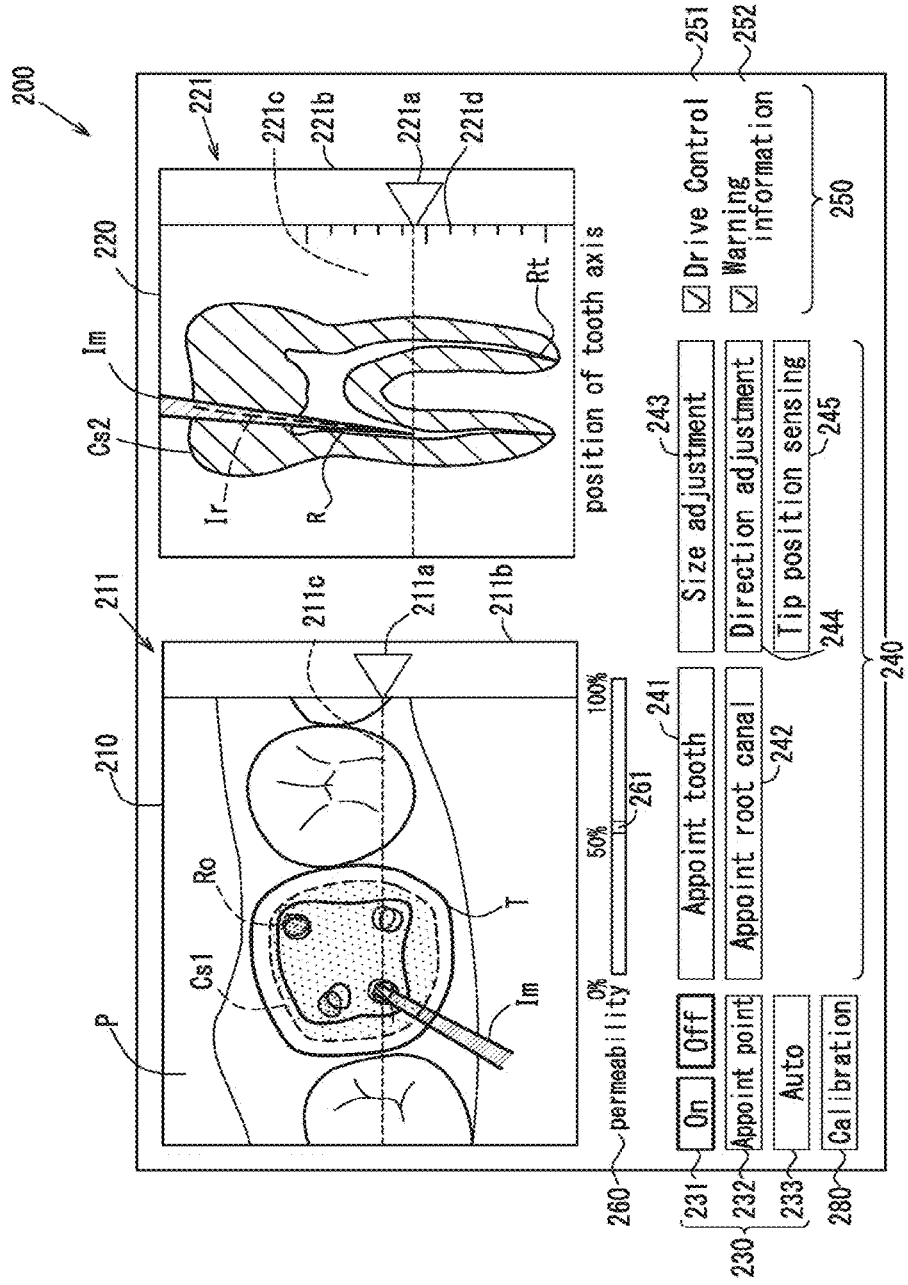

ROOT CANAL TREATING DEVICE

CROSS-REFERENCE TO RELATED APPLICATIONS

The present application is a continuation of and claims the benefit of priority to International Application No. PCT/JP2015/065231, filed May 27, 2015, which is based upon and claims the benefit of priority to Japanese Patent Application No. 2014-109866, filed May 28, 2014. The entire contents of these applications are incorporated herein by reference.

BACKGROUND OF THE INVENTION

Field of the Invention

The present invention relates to a root canal treating device that displays a visible light image of a tooth captured by, for example, an optical camera, and a cross-sectional image generated by an X-ray CT image capturing device based on position information on a root canal treating hand piece, in an overlapping manner in correspondence with each other.

Description of Background Art

Japanese Laid-Open Patent Publication No. 2006-305203 describes an X-ray CT image capturing device canal orifice.

Japanese PCT National-Phase Laid-Open Patent Publication No. 2013-519479 describes a three-dimensional imaging device that displays points or lines showing the shape of a root canal on a cross-sectional image of a tooth acquired by an X-ray CT image capturing device.

Japanese Laid-Open Patent Publication No. 2011-30637 describes technology for treating a root canal.

The entire contents of these publications are incorporated herein by reference.

SUMMARY OF THE INVENTION

According to one aspect of the present invention, a root canal treatment apparatus includes a root canal treatment hand piece having a visible light camera which captures a visible light image of a tooth as a target of interest, and circuitry which detects a position of the root canal treating hand piece, and instructs display of three images corresponding to at least a tip position of a cutting tool attached to the root canal treating hand piece, an X-ray cross-sectional image of the tooth captured by X-ray CT image capturing beforehand, and the visible light image captured by the visible light camera such that the three images are displayed on a display in an overlapping manner in positional correspondence with one another, based on information on the position of the root canal treating hand piece detected by the circuitry.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 10A, 10B and 10C show a method for adjusting a converted two-dimensional image;

FIGS. 12A and 12B provide photographs with overlapping display;

FIG. 13 shows a display position adjustment scroll bar;

FIG. 15 shows display of a tip of a surgical operation tool on the image overlapping display screen.

DETAILED DESCRIPTION OF THE EMBODIMENTS

Figure 1:
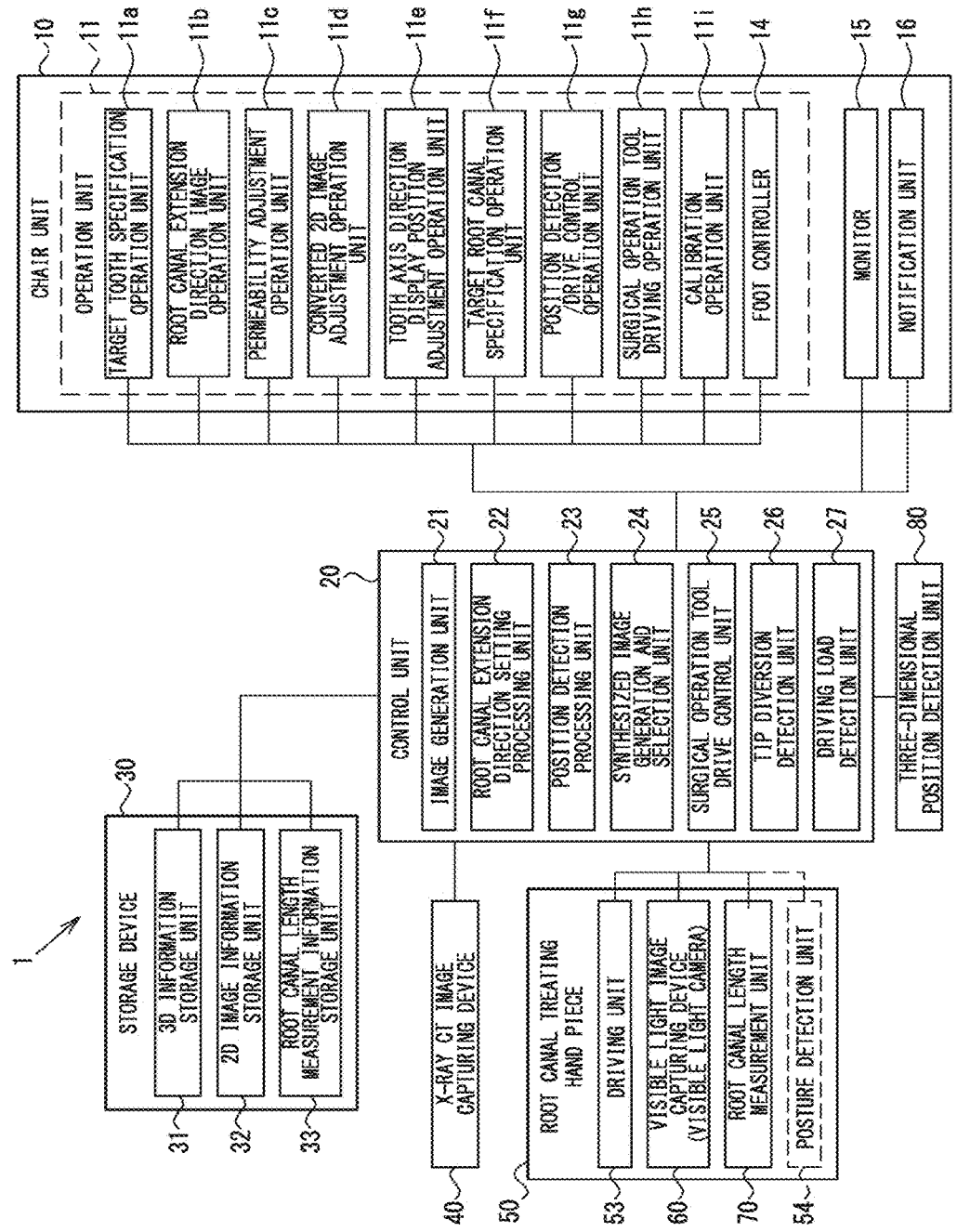
FIG. 1 is a block diagram of a medical care system according to an embodiment of the present invention.

The embodiments will now be described with reference to the accompanying drawings, wherein like reference numerals designate corresponding or identical elements throughout the various drawings.

A medical care system 1 according to an embodiment of the present invention is described with reference to FIG. 1 through FIG. 15.

Figure 2:
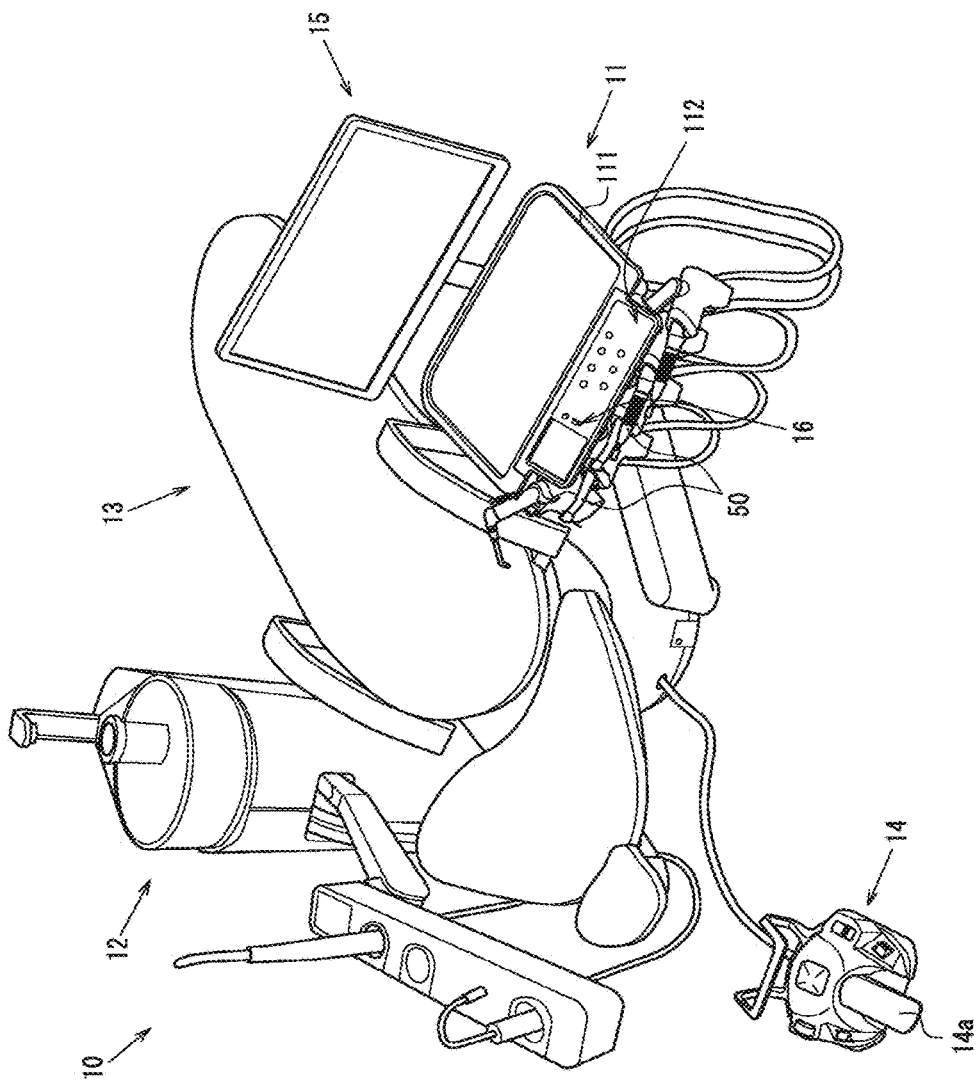
FIG. 2 is a schematic isometric view showing a structure of a chair unit.
Figure 3:
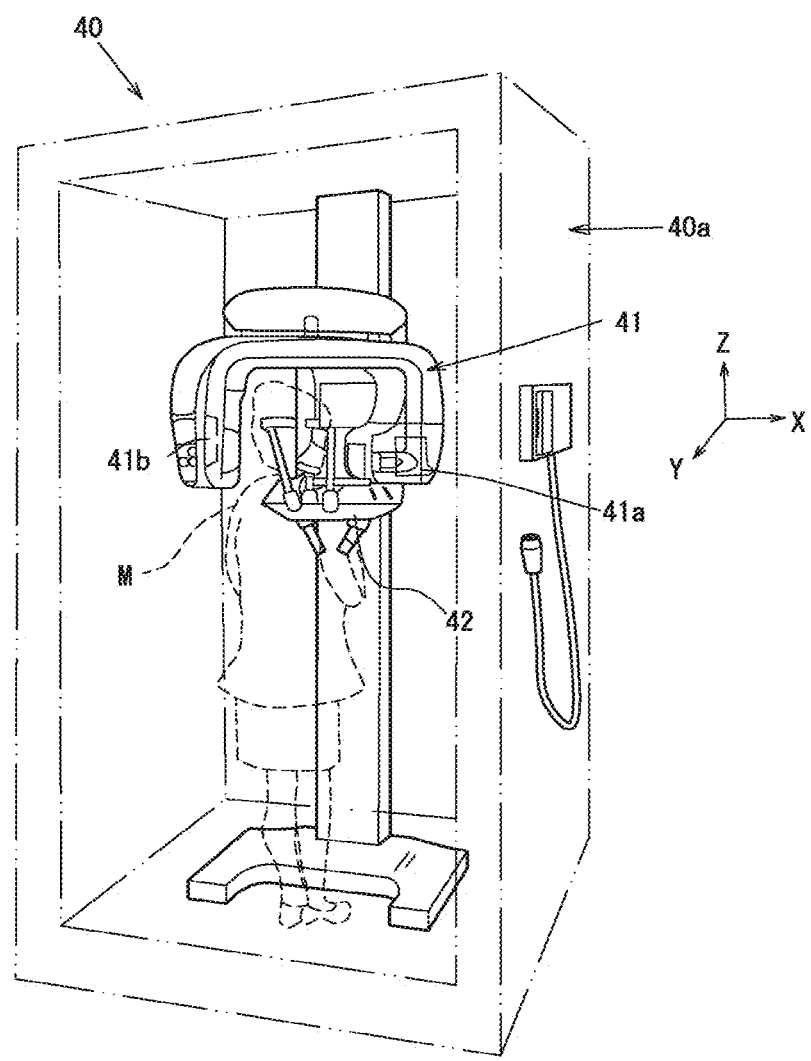
FIG. 3 is a schematic isometric view of an X-ray image capturing device.
Figure 4:
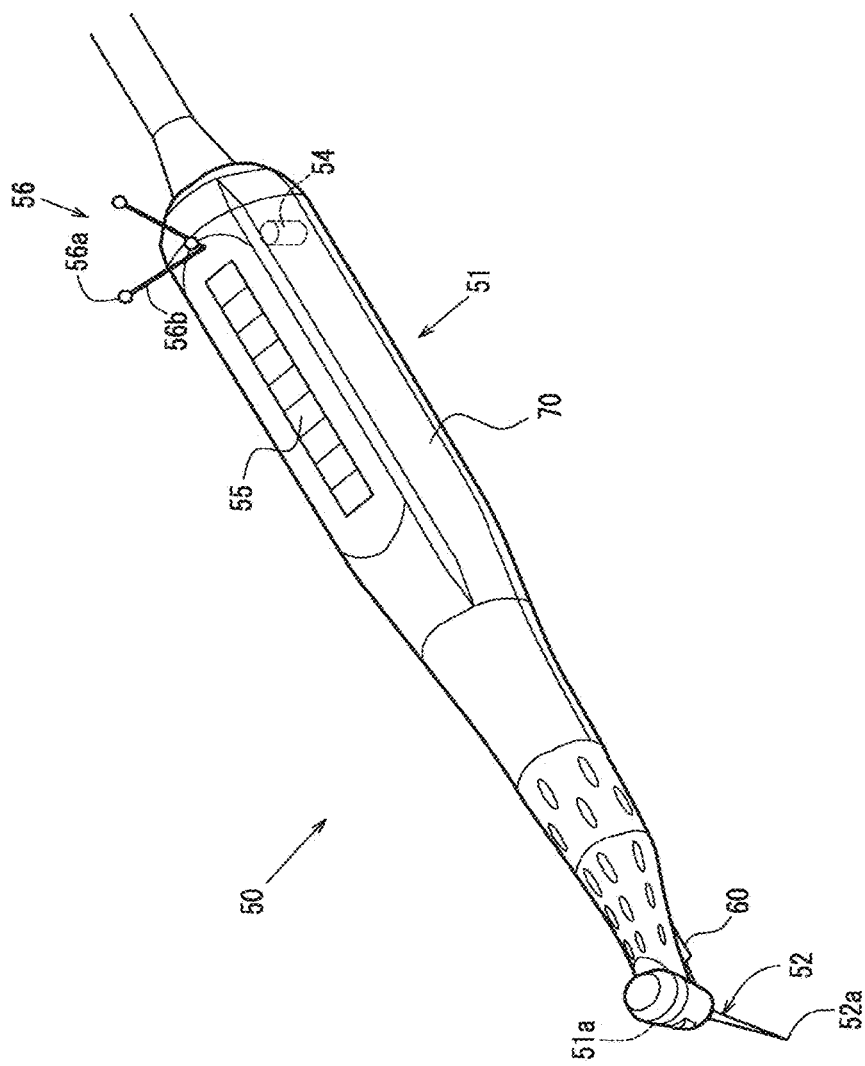
FIG. 4 is a schematic isometric view of a root canal treating hand piece in an embodiment according to the present invention.
Figure 5:
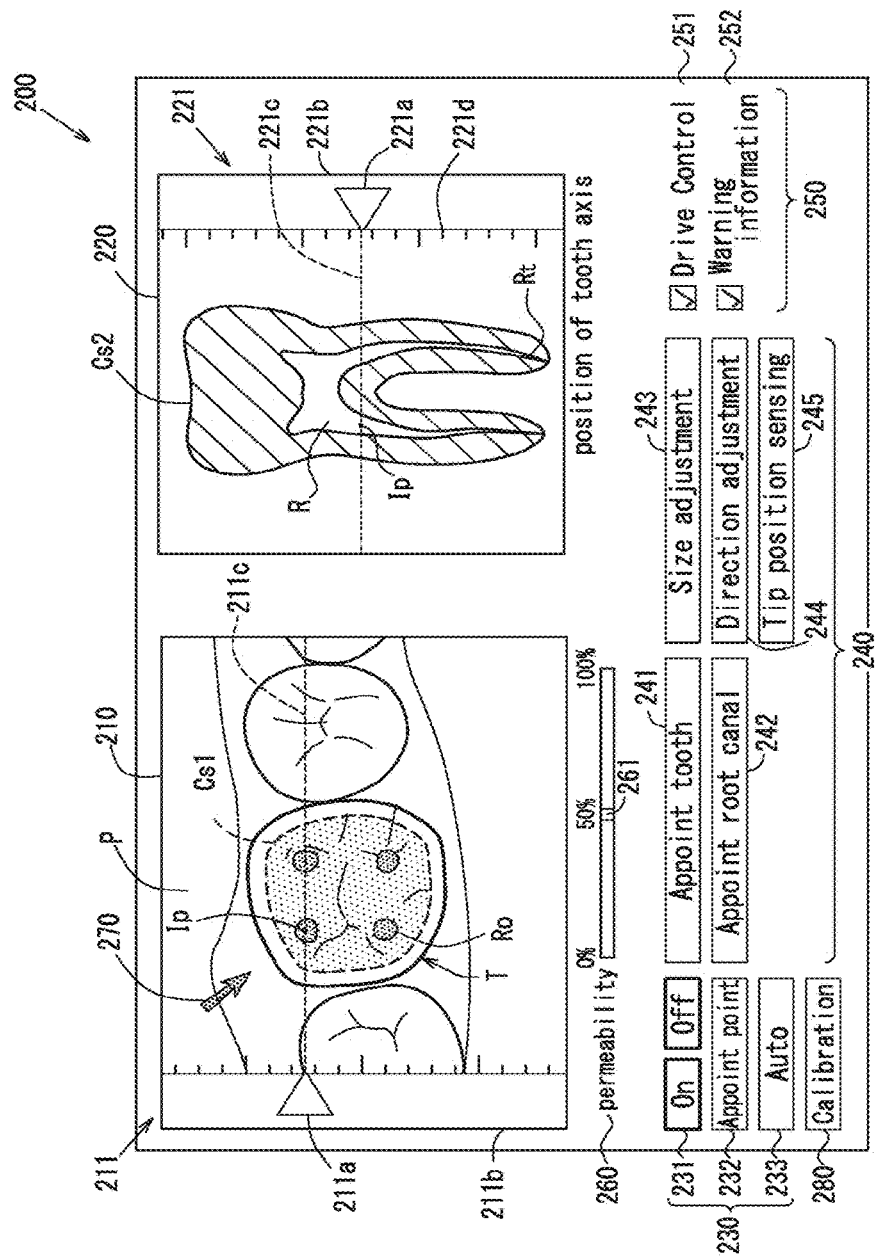
FIG. 5 shows an image overlapping screen.

FIG. 1 is a block diagram of the medical care system 1. FIG. 2 is a schematic isometric view showing a structure of a chair unit 10. FIG. 3 is a schematic isometric view of an X-ray CT image capturing device 40. FIG. 4 is a schematic isometric view of a root canal treating hand piece 50. FIG. 5 shows an image overlapping display screen 200.

Figure 6:
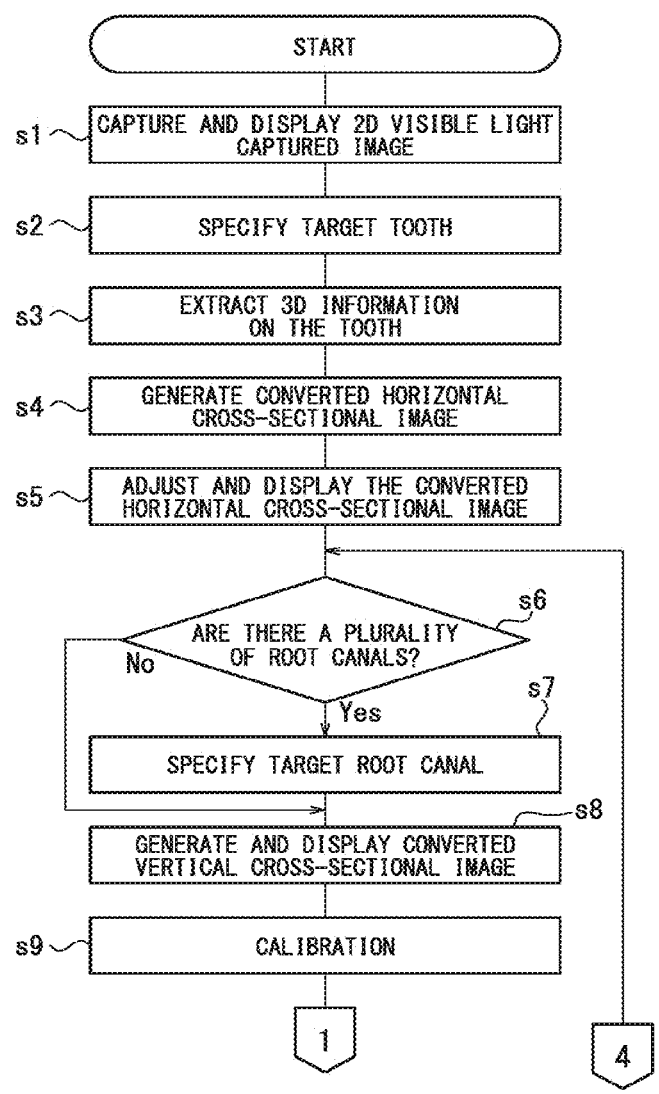
FIG. 6 is a flowchart showing a dental care process.
Figure 7:
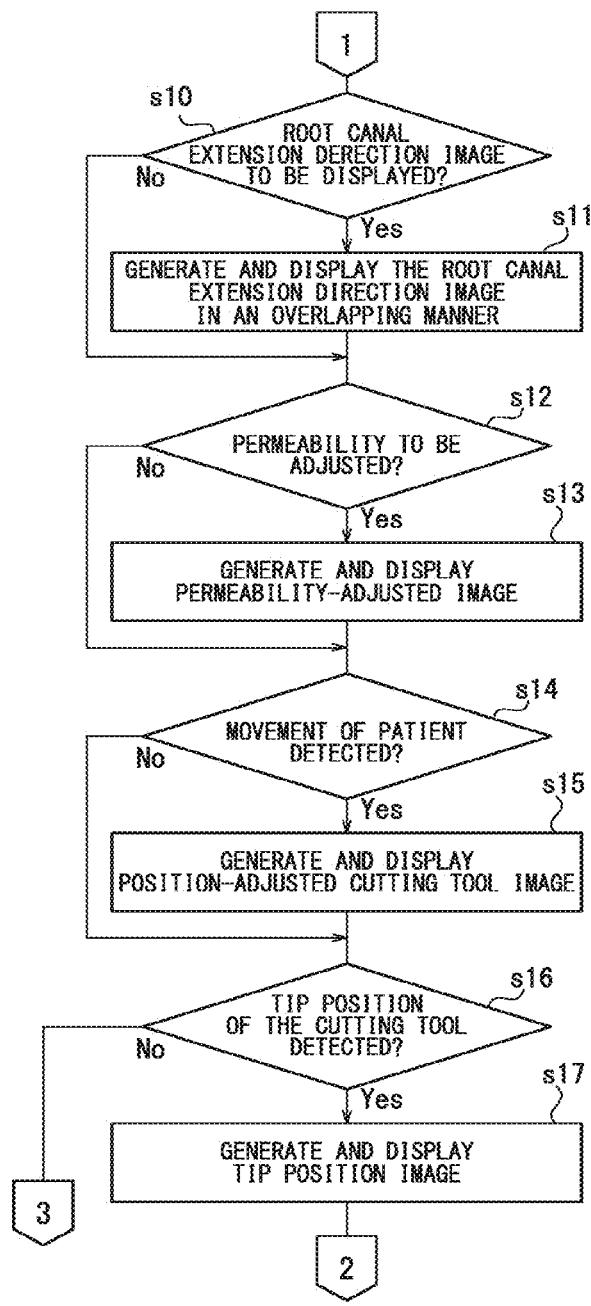
FIG. 7 is a flowchart showing the dental care process.
Figure 8:
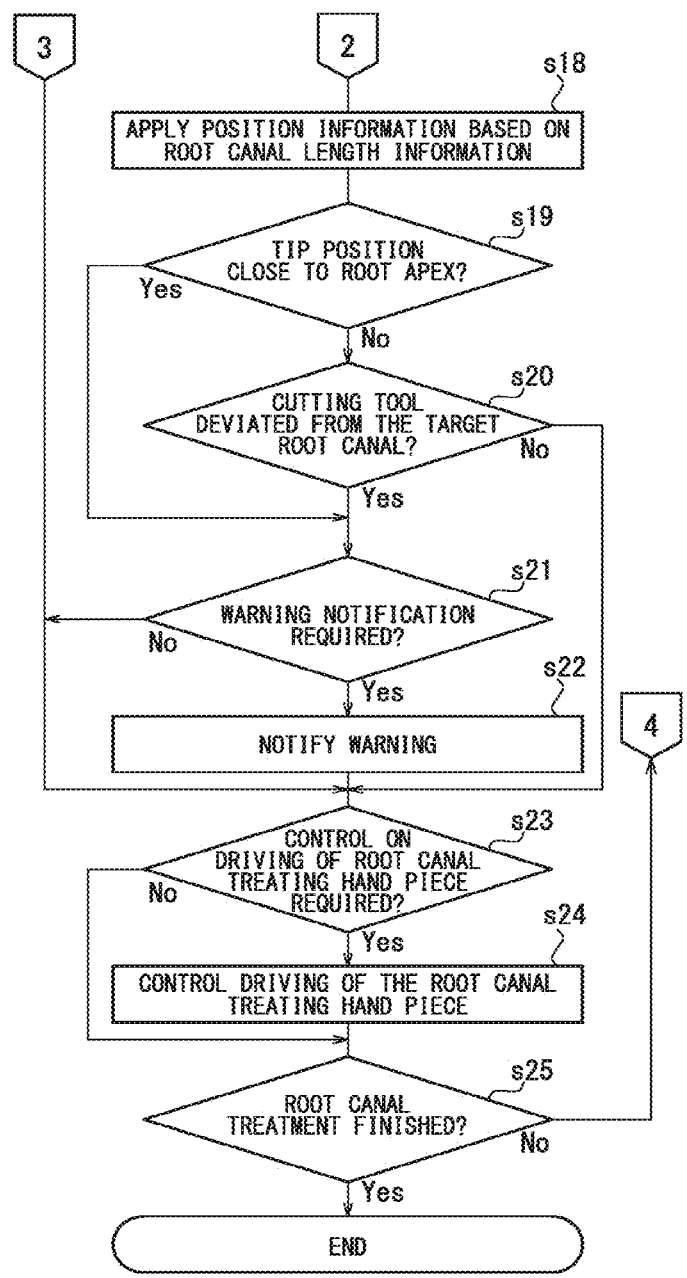
FIG. 8 is a flowchart showing the dental care process.
Figure 9:
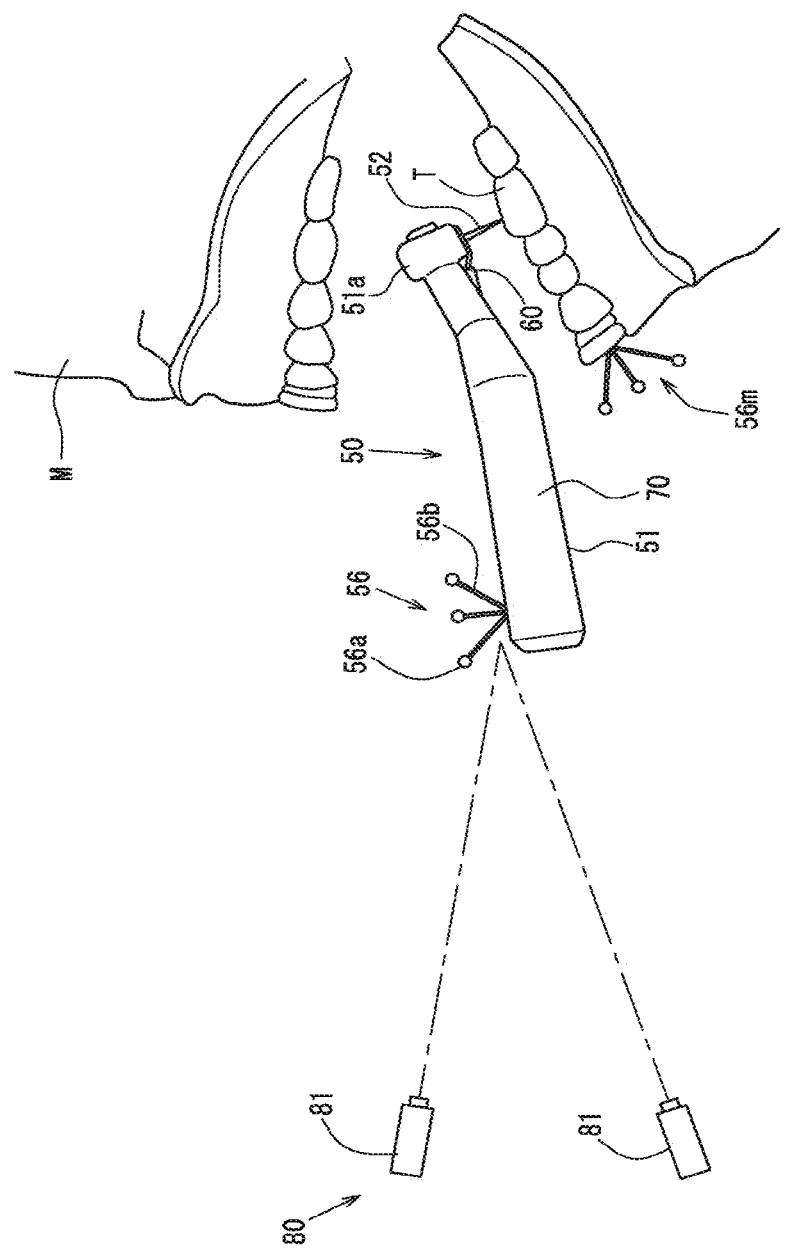
FIG. 9 is a schematic view showing three-dimensional position measurement.
Figure 11A:
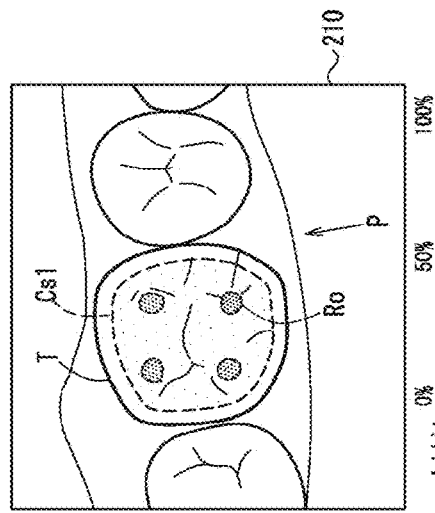
FIGS. 11A, 11B and 11C show a method for adjusting permeability.
Figure 11B:
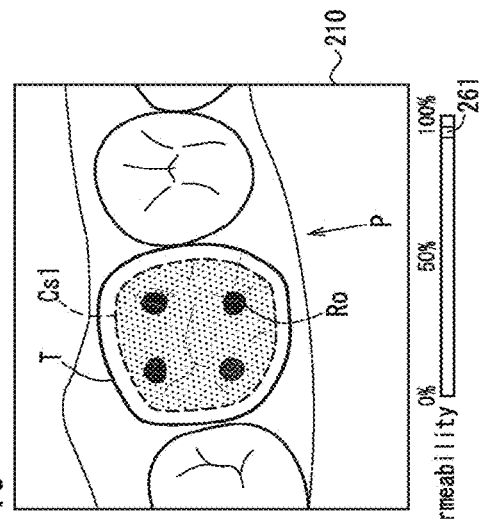
Figure 11C:
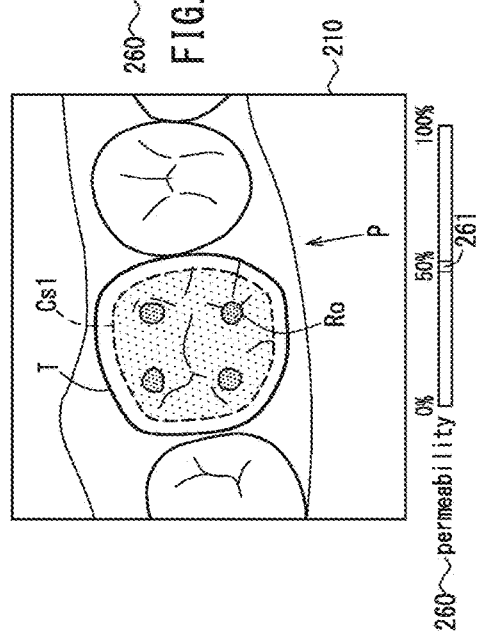

FIG. 6 through FIG. 8 are flowcharts showing a dental care process. FIG. 9 is a schematic view showing three-dimensional position measurement. FIGS. 10A, 10B and 10C show a method for adjusting a converted two-dimensional image. FIGS. 11A, 11B and 11C show a method for adjusting permeability. FIGS. 12A and 12B provide photographs with overlapping display.

FIG. 13 shows a display position adjustment scroll bar 221 on the image overlapping display screen 200. FIGS. 14A, 14B, 14C and 14D show display position adjustment in a tooth axis direction. FIG. 15 shows display of a tip of a surgical operation tool on the image overlapping display screen 200.

As shown in FIG. 1, the medical care system 1 includes the chair unit 10, a control unit 20, a storage device 30, the X-ray CT image capturing device 40, the root canal treating hand piece 50, and a three-dimensional position detection unit 80.

The control unit 20 includes a CPU, a ROM and a RAM, and has the following functional elements described in detail below.

The control unit 20 includes an image generation unit 21, a root canal extension direction setting processing unit 22, a position detection processing unit 23, a synthesized image generation and selection unit 24, a surgical operation tool drive control unit 25, a tip diversion detection unit 26, and a driving load detection unit 27. In FIG. 1, the control unit 20 is provided separately from the root canal treating hand piece 50. Alternatively, the control unit 20 may be included in the root canal treating hand piece 50.

The image generation unit 21 generates various types of images. Specifically, the image generation unit 21 converts three-dimensional information acquired by the X-ray CT image capturing device 40 into a two-dimensional image on a predetermined plane to generate a converted cross-sectional image (Cs), and also generates a 2D captured image (P) based on information captured by a visible light camera 60.

The root canal extension direction setting processing unit 22 sets a root canal extension direction running along a root canal (R) and passing a root canal orifice (Ro), and generates a root canal extension direction image (Id) (see FIG. 13).

The position detection processing unit 23 operates as follows. The position of the root canal treating hand piece 50 is detected by the three-dimensional position detection unit 80 by use of a three-dimensional position measurement marker 56 described later, and the position of a tool tip (52a) of a cutting tool 52 with respect to a root apex (Rt) is detected by a root canal length measurement unit 70. Based on the detection result, the position detection processing unit 23 generates and displays, at an appropriate position, a cutting tool tip position image (Ip) or a cutting tool image (Im) described later.

The synthesized image generation and selection unit 24 positionally aligns and synthesizes three images, namely, a converted horizontal cross-sectional image (Cs1) and the 2D captured image (P) generated by the image generation unit 21 and the cutting tool tip position image (Ip) or the cutting tool image (Im) generated by the position detection processing unit 23. Thus, the synthesized image generation and selection unit 24 generates a synthesized image of the three images, and also generates a synthesized image of the three images and the root canal extension direction image (Id). The surgical operation tool drive control unit 25 controls driving of the root canal treating hand piece 50.

The tip diversion detection unit 26 detects a diversion of the cutting tool 52 attached to the root canal treating hand piece 50 from the root canal (R). The driving load detection unit 27 detects a driving load on the root canal treating hand piece 50.

The storage device 30 includes an HDD, an SSD or the like, and includes the following functional elements. The storage device 30 includes a 3D information storage unit 31 that stores the three-dimensional information (hereinafter, referred to as "3D information") acquired by the X-ray CT image capturing device 40, a 2D image information storage unit 32 that stores two-dimensional image information (hereinafter, referred to as "2D image information") captured with visible light by the visible light camera 60, and a root canal length measurement information storage unit 33 that stores root canal length measurement information such as a root canal length or the like measured by the root canal length measurement unit 70.

As shown in FIG. 2, the chair unit 10 includes an operation unit 11, a basin unit 12 including a suction device that sucks saliva, cooled water or the like and a device usable to gargle, a medical care chair 13 including a reclining back sheet and an up/down movable seat, a foot controller 14 that is connected to the medical care chair 13, a monitor 15, a notification unit 16. The root canal treating hand piece 70 may be attached to a holder of the chair unit 10 (root canal treating hand pieces 50 are shown in FIG. 2).

As shown in FIG. 2, the operation driving unit 11 includes various types of operation devices 112 located on a tray table 111 provided at a top surface of the operation driving unit 11. The root canal treating hand piece 50 attached to the holder provided forward to the operation devices 112, and a display screen displayed on the monitor 15 provided on a rear side of the operation driving unit 11, are operated by use of these operation devices 112.

The operation devices 112 include a touch screen, a pointing stick and the like. The operation devices 112 may include an input device such as a mouse or the like.

The operation unit 11 is described more specifically. The operation unit 11 includes the following functional elements in addition to the foot controller 14 including a pedal (14a) operable by a foot of an operator. It can be detected that the pedal (14a) has been stepped on as well as the amount of stepping. The functional elements included in the operation driving unit 11 include a target tooth specification operation unit (11a), a root canal extension direction image operation unit (11b), a permeability adjustment operation unit (11c), a converted 2D image adjustment operation unit (11d), a tooth axis direction display position adjustment operation unit (11e), a target root canal specification operation unit (11f), a position detection/drive control operation unit (11g), a surgical operation tool driving operation unit (11h), and a calibration operation unit (11i).

The target tooth specification operation unit (11a) specifies a tooth (T) as a target of a surgical operation from the 2D captured image (P) captured by the visible light camera 60 described later, and extracts 3D information on the tooth (T) from multiple pieces of 3D information stored on the 3D information storage unit 31.

The root canal extension direction image operation unit (11b) sets and displays the root canal extension direction image (Id) on the image overlapping display screen 200 described later with reference to FIG. 5.

The permeability adjustment operation unit (11c) adjusts the permeability of the converted horizontal cross-sectional image (Cs1) displayed as overlapping the 2D captured image (P), and the permeability of an X-ray CT image of a horizontal cross-section of the tooth (T) taken along a plane perpendicular to the tooth axis direction. The adjustment on the permeability is performed on the image overlapping display screen 200 described later.

The converted 2D image adjustment operation unit (11d) adjusts the size and the orientation of the converted cross-sectional image (Cs), converted from the 3D information acquired by the X-ray CT image capturing device 40, with respect to the 2D captured image (P) captured by the visible light camera 60.

The tooth axis direction display position adjustment operation unit (11e) sets a desired depth in the tooth axis direction at which the converted horizontal cross-sectional image (Cs1) is to be displayed as overlapping the 2D captured image (P) on the image overlapping display screen 200 described later with reference to FIG. 5.

The target root canal specification operation unit (11f) specifies a root canal (R) as a target of the surgical operation from the converted horizontal cross-sectional image (Cs1), and reads 3D information on the root canal (R) based on the 3D information, extracted from the 3D information storage unit 31, on the tooth (T) specified by the target tooth specification operation unit (11a).

The position detection/drive control operation unit (11g) makes, for example, the following instructions. The position detection/drive control operation unit (11g) instructs the three-dimensional position detection unit 80 or the root canal length measurement unit 70 to detect the position of the tool tip (52a) of the cutting tool 52 attached to the root canal treating hand piece 50 used for the surgical operation performed on the tooth (T). The position detection/drive control operation unit (11g) controls such that based on the detection result, the cutting tool tip position image (Ip) or the cutting tool image (Im) described later are displayed at an appropriate position on the image overlapping display screen 200 (see FIGS. 14A, 14B, 14C and 14D). The position detection/drive control operation unit (11g) instructs the notification unit 16 to make a notification. The position detection/drive control operation unit (11g) instructs a driving unit 53 described later to drive the root canal treating hand piece 50.

The surgical operation tool driving operation unit 11h switches the root canal treating hand piece 50 described later to be on or off, and adjusts an output of the root canal treating hand piece 50.

The calibration operation unit (11i) performs an initialization process on a position of the tool tip (52a) of the cutting tool 52 with respect to the tooth (T).

The foot controller 14 is usable to make an appropriate operation of, for example, confirming the operation selected by use of the operation unit 11 or selecting an operation instead of the operation unit 11.

The operation units (11a through 11i) described above are operable by use of the various types of operation devices 112 or the image overlapping display screen 200.

The notification unit 16 operates as follows. The three-dimensional position detection unit 80 or the root canal length measurement unit 70 detects that the tool tip (52a) of the cutting tool 52 attached to the root canal treating hand piece 50 is close to the root apex (Rt). Based on an output from the three-dimensional position detection unit 80 or the root canal length measurement unit 70, namely, when the tool tip (52a) of the cutting tool 52 is close to the root apex (Rt) to a certain degree, the notification unit 16 makes a notification by use of voice, buzzer, light or the like.

As shown in FIG. 3, the X-ray CT image capturing device 40 is accommodated in a hollow parallelepiped X-ray-proof chamber (40a) longer in a height direction, and executes CT image capturing to collect projection data. The X-ray CT image capturing device 40 includes a revolving arm 41 which supports an X-ray generation unit (41a) and an X-ray detection unit (41b) such that the X-ray generation unit (41a) and the X-ray detection unit (41b) face each other. The revolving arm 41 is movable up and down along a support pillar and is revolvable. The X-ray generation unit (41a) emits an X-ray cone beam toward a patient (M), and the X-ray detection unit (41b) detects the X-ray cone beam emitted by the X-ray generation unit (41a).

The X-ray CT image capturing device 40 having such a structure operates as follows. The patient (M) is located as being held between the X-ray generation unit (41a) and the X-ray detection unit (41b) supported by the revolving arm 41. While the revolving arm 41 revolves around the patient (M), the X-ray cone beam emitted by the X-ray generation unit (41a) and transmitted through the patient (M) is detected by the X-ray detection unit (41b). Thus, 3D information is acquired.

The X-ray CT image capturing device 40 is connected to the storage device 30 via the control unit 20, and thus the 3D information acquired by the X-ray CT image capturing device 40 is stored on the 3D information storage unit 31 of the storage device 30.

As shown in FIG. 4, the root canal treating hand piece 50 has the cutting tool 52, which is rotatable, attached to a head (51a) at a tip thereof. The rotatable cutting tool 52 is replaceable. The root canal treating hand piece 50 includes a hand piece main body 51, the driving unit 53 such as a micromotor or the like that drives the cutting tool 52 to rotate, a control unit (not shown), and the root canal length measurement unit 70. The driving unit 53, the control unit, and the root canal length measurement unit 70 are accommodated in the hand piece main body 51. The root canal treating hand piece 50 is connected to an oral cavity electrode (not shown) by a connection cable (not shown) provided at a rear end thereof.

The root canal treating hand piece 50 has the visible light camera 60 attached to the head (51a). The root canal treating hand piece 50 includes a measurement result display unit 55 that displays a measurement result acquired by the root canal length measurement unit 70 described later, and a three-dimensional position measurement marker 56. The measurement result display unit 55 is located on a top surface of a rear part of the hand piece main body 51, and the three-dimensional position measurement marker 56 protrudes in three upward directions from the top of surface of the rear part of the hand piece main body 51.

The three-dimensional position measurement marker 56 includes three targets (56a) located so as to make a triangle in a space, and three arms (56b) having the targets (56a) fixed at tips thereof. The three arms (56b) and the targets (56a) stand on the hand piece main body 51 so as to cross one another.

The root canal treating hand piece 50 having such a structure is driven by the surgical operation tool driving operation unit (11h) via surgical operation tool drive control unit 25 provided inside the hand piece main body 51, and thus cuts off a decayed part or a contaminated root canal wall of the tooth (T) as the surgical operation target. The surgical operation tool drive control unit 25 may be located at another position (not shown) connected to the hand piece main body 51. The hand piece main body 51 may be formed of a cordless hand piece.

The root canal length measurement unit 70 measures, based on an electric current value or the like, the position of the tool tip (52a) of the cutting tool 52 with respect to the root apex (Rt), which is the tip of the root canal (R) of the tooth (T). The root canal length measurement unit 70 supplies an electric current between the cutting tool 52 attached to the head (51a) and the oral cavity electrode (not shown), which is a hook-shaped electrode that is hooked at a corner of the mouth of the patient (M), and measures how close the tool tip (52a) of the cutting tool 52 is to the root apex (Rt) and thus measures the length of the root canal (R).

Specifically, the root canal length measurement unit 70 may operate in the following manner. The oral cavity electrode is hooked at a corner of the mouth of the patient (M), while the cutting tool 52 is inserted into the root canal (R) of the tooth (T). The position of the tool tip (52a) of the cutting tool 52 with respect to the root apex (Rt) of the root canal (R) of the tooth (T) is measured based on an electric current value.

The measurement result acquired by the root canal length measurement unit 70 is displayed by the measurement result display unit 55 provided on the hand piece main body 51, and is stored on the root canal length measurement information storage unit 33 of the storage device 30.

The measurement result acquired by the root canal length measurement unit 70 is used to detect a three-dimensional position of the root canal treating hand piece 50 in an area from the root canal orifice (Ro) to the root apex (Rt). Generally in this area, the root canal (R) is curved. Since the cutting tool 52 advances along the curved root canal (R), it is important to use the measurement result acquired by the root canal length measurement unit 70 that shows a distance from the tool tip (52*a*) of the cutting tool 52 to the root apex (Rt).

The visible light camera 60, which acts as an example of visible light image capturing device, is located on a neck part at a base of the head (51*a*) of the root canal treating hand piece 50. The visible light camera 60 directs illumination light from the head (51*a*) inserted into the oral cavity of the patient (M) toward an image capturing target site, which is an area of interest, and receives the light reflected by the image capturing target site by a solid-state image capturing sensor (not shown) such as a CMOS or the like to capture the 2D captured image (P). The 2D captured image (P) captured by the visible light camera 60 is stored on the 2D image information storage unit 32 of the storage device 30.

As the visible light image capturing device, a microscope may be used.

The three-dimensional position detection unit 80 includes a pair of infrared position detection cameras 81 (see FIG. 9) that capture an image of the targets (56*a*) of the three-dimensional position measurement marker 56 provided on the hand piece main body 51. A digital image captured by the three-dimensional position detection unit 80 is binarized by the position detection processing unit 23. The position detection processing unit 23 calculates a three-dimensional position of each of the targets (56*a*) to obtain a three-dimensional position of the measurement target.

Alternatively, the root canal treating hand piece 50 may include a posture detection unit 54 (represented by dashed line in FIG. 1) instead of the three targets (56*a*). The posture detection unit 54 measures a three-dimensional position of one point on the hand piece main body 51, and includes a gyrosensor. In this case, the three-dimensional position and the posture of the root canal treating hand piece 50 may be measured.

Still alternatively, a reflective plate may be used instead of the targets (56*a*). In this case, a laser light beam may be directed and reflected by the reflective plate, so that the reflected light beam is measured to find the three-dimensional position. Still alternatively, the three-dimensional position detection unit 80 may include an infrared light sensor detection unit that detects a position by use of infrared light reflected by the reflective plate, a magnetic field generation unit and a magnetic field detection unit, or a radio wave detection unit that detects a position by use of a radio wave signal transmitted from a radio wave transmission device. Anyway, in a surgical operation performed on a tooth crown up to the root canal orifice (Ro) or a pulp chamber up to the root canal orifice (Ro), a non-contact three-dimensional position detection unit detects the three-dimensional position of the root canal treating hand piece 50 safely and accurately.

As described above, any non-contact three-dimensional position detection unit may be used as the three-dimensional position detection unit 80. As the position detection unit, the root canal length measurement unit 70 described above may be used instead of the non-contact three-dimensional position detection unit 80.

This is described in more detail. For an area from the tooth crown to the root canal orifice (Ro), the non-contact three-dimensional position detection unit 80 is usable. For an area from the root canal orifice (Ro) to the root apex (Rt), the root canal length measurement unit 70 is usable. Either the detection result acquired by the root canal length measurement unit 70 or the detection result acquired by the three-dimensional position detection unit 80 may be selected to be used in accordance with the shape of the root canal (R) or the type of the cutting tool 52.

Based on the three-dimensional position of the root canal treating hand piece 50 detected by the three-dimensional position detection unit 80 as described above, the three-dimensional position of the tool tip (52*a*) of the cutting tool 52 is detected by the position detection processing unit 23.

With reference to FIG. 5, the image overlapping display screen 200 displayed on the monitor 15 in the medical care system 1 is described.

The image overlapping display screen 200 displayed on the monitor 15 includes an occlusal surface direction image display area 210 located in an upper left part, a vertical cross-sectional image display area 220 located in an upper right part, a root canal extension direction image operation unit 230 located in a lower left part, various types of selection operation units 240 located in a lower central part, a command check box unit 250 located in a lower right part, a permeability adjustment scroll bar 260 displayed between the occlusal surface direction image display area 210 and the root canal extension direction image operation unit 230 and acting as the permeability adjustment operation unit (11*c*), a calibration specification operation unit 280 acting as the calibration operation unit (11*i*), and a cursor 270 operable by a pointing device among the various types of operation devices 112 (when operated by a mouse, the cursor 270 is occasionally referred to as a "mouse pointer" or simply as a "pointer").

The occlusal surface direction image display area 210 displays, in an overlapping manner, three images, namely, the 2D captured image (P) captured by the visible light camera 60 attached to the head (51*a*) and stored on the 2D image information storage unit 32, the converted horizontal cross-sectional image (Cs1), and the cutting tool tip position image (Ip) showing the position of the tool tip (52*a*) of the cutting tool 52, and also displays a synthesized image of these images generated by the image generation unit 21. The occlusal surface direction image display area 210 includes a cross-sectional position adjustment scroll bar 211 usable to accept an operation of making a setting such that a converted vertical cross-sectional image (Cs2) to be displayed in the vertical cross-sectional image display area 220 is of a desired position of the tooth (T).

The converted horizontal cross-sectional image (Cs1) displayed in the occlusal surface direction image display area 210 as overlapping the 2D captured image (P) of the occlusal surface of the tooth (T) captured in the tooth axis direction is a cross-sectional image based on three-dimensional image capturing data on the tooth (T) captured by the X-ray CT image capturing beforehand, and is an X-ray cross-sectional image along a plane in the horizontal direction of a position of tooth (T) specified by a knob (221*a*) displayed in the vertical cross-sectional image display area 220 described later. In the occlusal surface direction image display area 210, the 2D captured image (P) and the converted horizontal cross-sectional image (Cs1) are positioned with respect to each other based on outlines thereof or the like and are displayed in an overlapping manner as shown in FIG. 5. The overlapping display allows the converted horizontal cross-sectional image (Cs1) to be displayed on the 2D captured image (P) and allows the root canal orifice (Ro) to be visually recognized. Therefore, the operator can perform cutting toward the root canal orifice (Ro). These images displayed in an overlapping manner may be still images or moving images.

This is described in more detail. A knob (211a) in an arrow (211b) of the cross-sectional position adjustment scroll bar 211 is operated by the cursor 270 to set the cross-sectional position of the tooth (T) at which the converted vertical cross-sectional image (Cs2) is to be displayed in the vertical cross-sectional image display area 220. The knob (211a) provides a cross-section display line (211c), which specifies such a cross-sectional position.

The above-described cross-sectional position is set by holding and moving the cross-section display line (211c) to a desired position by a so-called drag-and-drop operation made on the cursor 270. The arrow (211b) and the knob (211a) may be omitted, so that the cross-section display line (211c) is directly held and moved.

The vertical cross-sectional image display area 220 displays the converted vertical cross-sectional image (Cs2) at the cross-sectional position, specified by the cross-section display line (211c), of the tooth (T) that is set by the target tooth specification operation unit (11a) shown in FIG. 1. In addition, the vertical cross-sectional image display area 220 includes a display position adjustment scroll bar 221 usable to accept an operation of making a setting such that the converted horizontal cross-sectional image (Cs1) to be displayed in the occlusal surface direction image display area 210 is of a desired position of the tooth (T) in the tooth axis direction.

The display position adjustment scroll bar 221 sets, by use of the knob (221a), a desired cross-section display position of the tooth (T) in the tooth axis direction at which the converted horizontal cross-sectional image (Cs1) is to be displayed in the occlusal surface direction image display area 210. Thus, the display position adjustment scroll bar 221 acts as the tooth axis direction display position adjustment operation unit (11e).

This is described in more detail. The knob (221a) in an arrow (221b) of the display position adjustment scroll bar 221 is operated by the cursor 270 to set the display position of the tooth (T) in the tooth axis direction at which the converted horizontal cross-sectional image (Cs1) is to be displayed in the occlusal surface direction image display area 210. The knob (221a) provides a cross-section display line (221c), which specifies such a display position. As shown in FIG. 5, the cross-section display line (221c) is in the vicinity of the center of the tooth (T) in the tooth axis direction, namely, in a top part of the root canal (R), in a default setting.

The vertical cross-sectional image display area 220 also includes a scale (221d) along the arrow (221b). The scale (221d) shows a distance from the cross-section display line (221c) to the root apex (Rt). The arrow (221b) and the knob (221a) may be omitted, so that the cross-section display line (221c) is directly held and moved, like in the case of the cross-sectional position adjustment scroll bar 211.

The converted vertical cross-sectional image (Cs2) to be displayed in the vertical cross-sectional image display area 220 is generated based on the 3D information, acquired by the X-ray CT image capturing device 40, on the tooth (T) set by the target tooth specification operation unit (11a) shown in FIG. 1.

As an image of a cross-section taken along the tooth axis direction that is to be displayed in the vertical cross-sectional image display area 220, the converted vertical cross-sectional image (Cs2) is generated as follows. The 3D information on the tooth (T) that is stored on the 3D information storage unit 31 of the storage device 30 is read, and the converted vertical cross-sectional image (Cs2) of the cross-section specified by the cursor 270 (the cross-section shown in FIG. 5 passes the cutting tool tip position image (Ip) of the root canal (R)) is generated by the image generation unit 21 and displayed in the occlusal surface direction image display area 210.

In FIG. 5, the converted vertical cross-sectional image (Cs2) is of the cross-section of the tooth (T) that is specified by the cross-section display line (211c) displayed in the occlusal surface direction image display area 210. The converted vertical cross-sectional image (Cs2) is generated by the image generation unit 21 based on the 3D information stored on the 3D information storage unit 31 and is displayed in the vertical cross-sectional image display area 220.

The converted horizontal cross-sectional image (Cs1) is of a cross-section which is parallel to the occlusal surface and is specified by the cross-section display line (221c). The converted horizontal cross-sectional image (Cs1) is generated by the image generation unit 21 based on the 3D information stored on the 3D information storage unit 31 and is displayed as overlapping the 2D captured image (P) in the occlusal surface direction image display area 210. The display is made after the converted horizontal cross-sectional image (Cs1) is positionally adjusted to the 2D captured image (P). Herein, the expression "adjust" specifically encompasses rotation, magnification adjustment and positional adjustment of the image as described in more detail later.

The cutting tool tip position image (Ip) shows the position of the tool tip (52a) of the cutting tool 52 that is detected by the root canal length measurement unit 70 or the three-dimensional position detection unit 80. Therefore, when a tip position sensing selection unit 245 described later is operated, the converted horizontal cross-sectional image (Cs1) and the converted vertical cross-sectional image (Cs2) corresponding to the position of the cutting tool tip position image (Ip) are automatically displayed together the cutting tool tip position image (Ip). Therefore, the operator can perform a surgical operation while checking the position of the tool top (52a) of the cutting tool 52 in real time. This allows the operator to perform the surgical operation accurately without the tool top (52a) of the cutting tool 52 coming off from the root canal (R) or piercing the root apex (Rt). In FIG. 5, the cutting tool tip position image (Ip) showing the tool tip (52a) of the cutting tool 52 is a dotted image. Alternatively, the cutting tool tip position image (Ip) may be a blinking dotted image or may be an image showing a part of, or the entirety of, the cutting tool 52.

The root canal extension direction image operation unit 230 acts as the root canal extension direction image operation unit (11b). For example, the root canal extension direction image operation unit 230 includes various types of selection units each provided in the form of a touch panel. In more detail, the root canal extension direction image operation unit 230 includes an ON/OFF switching selection unit 231 usable to select whether or not to display the root canal extension direction image (Id), an appoint point specification unit 232 usable to specify an arbitrary point to set the root canal extension direction image (Id), and an "auto" specification unit 233 usable to automatically set the root canal extension direction image (Id). In the case where the "auto" specification unit 233 is operated, the position of the root canal (R) that is being cut currently is specified by the knob (221a) in FIG. 5, so that the direction in which an area of several millimeters of the root canal (R) that is close to the root apex (Rt) is curved is always shown in correspondence with the advancement of the cutting tool 52.

The ON/OFF switching selection unit 231 is usable to select whether or not to display the root canal extension direction image (Id) as overlapping the converted horizontal cross-sectional image (Cs1) or the converted vertical cross-sectional image (Cs2) in the occlusal surface direction image display area 210 or the vertical cross-sectional image display area 220 of the image overlapping display screen 200. The ON/OFF switching selection unit 231 allows either ON or OFF to be selected.

The appoint point specification unit 232 is usable to accept a selected arbitrary point on the root canal (R) in the converted vertical cross-sectional image (Cs2) displayed in the vertical cross-sectional image display area 220. The appoint point specification unit 232 acts as the root canal extension direction image operation unit (11b).

Either one of the appoint point specification unit 232 and the "auto" specification unit 233 is selectively operable. The "auto" specification unit 233 is usable to specify that the root canal (R) in the converted vertical cross-sectional image (Cs2) displayed in the vertical cross-sectional image display area 220 is to be recognized by image recognition to automatically set and display the root canal extension direction image (Id) passing the root canal orifice (Ro).

The various types of selection operation units 240 include an appoint tooth selection unit 241, an appoint root canal selection unit 242, a size adjustment selection unit 243, an orientation adjustment selection unit 244, and a tip position sensing selection unit 245. In the example of FIG. 5, the selection units are each provided in the form of a touch screen in a liquid crystal display unit. Alternatively, the selection units may each be provided in the form of hardware such as a pushbutton switch or the like.

The appoint tooth selection unit 241 acts as the target tooth specification operation unit (11a). After an operation is made on the appoint tooth selection unit 241, the tooth (T) which is a surgical operation target is specified from the 2D captured image (P) displayed in the occlusal surface direction image display area 210. The specification is made by the cursor 270 through an operation made on the pointing device among the various types of operation devices 112. Thus, the tooth (T) which is the surgical operation target is set among teeth (T) displayed in the 2D captured image (P).

The appoint root canal selection unit 242 acts as the target root canal specification operation unit (11f). After an operation is made on the appoint root canal selection unit 242, the root canal orifice Ro which is a surgical operation target is specified from the converted horizontal cross-sectional image (Cs1) displayed in the occlusal surface direction image display area 210 in an overlapping manner. The specification is made by the cursor 270 through an operation made on the pointing device among the various types of operation devices 112. Thus, the root canal orifice (Ro) which is the surgical operation target is set among the root canal orifices (Ro) displayed in the converted horizontal cross-sectional image (Cs1).

The size adjustment selection unit 243 acts as the converted 2D image adjustment operation unit (11d) together with the orientation adjustment selection unit 244 described later. The size adjustment selection unit 243 is an instruction unit usable to adjust the size of the converted horizontal cross-sectional image (Cs1), of the tooth (T) specified as the target tooth, generated by the image generation unit 21 based on the 3D information extracted from the 3D information storage unit 31. The size adjustment is performed with respect to the size of the tooth (T) to be displayed in the 2D captured image (P) in the occlusal surface direction image display area 210.

The orientation adjustment selection unit 244 acts as the converted 2D image adjustment operation unit (11d) together with the size adjustment selection unit 243. The orientation adjustment selection unit 244 is an instruction unit usable to adjust the orientation of the converted horizontal cross-sectional image (Cs1), of the tooth (T) specified as the target tooth, generated by the image generation unit 21 based on the 3D information extracted from the 3D information storage unit 31. The orientation adjustment is performed with respect to the orientation of the tooth (T) to be displayed in the 2D captured image (P) in the occlusal surface direction image display area 210.

The tip position sensing selection unit 245 acts as the position detection/drive control operation unit (11g), and is an instruction unit usable to detect the position of the tool tip (52a) of the cutting tool 52 during a surgical operation performed on the tooth (T) by use of the root canal treating hand piece 50. The detection is performed by use of the three-dimensional position detection unit 80 or the root canal length measurement unit 70. When the position of the tool tip (52a) is detected, the tip position sensing selection unit 245 displays the converted cross-sectional images (Cs) and the cutting tool tip position image (Ip) or the cutting tool image (Im) in the occlusal surface direction image display area 210 and the vertical cross-sectional image display area 220, with the positions thereof being adjusted.

The command check box unit 250 includes a drive control check box 251 and a warning information check box 252.

The drive control check box 251 acts as the position detection/drive control operation unit (11g). The drive control check box 251 is to be checked to restrict the driving of the root canal treating hand piece 50 when, for example, the root canal treating hand piece 50 has been detected, by the driving load detection unit 27, to have been acted on by an excessive load, or when the tool tip (52a) of the cutting tool 52 is close to the root apex (Rt).

The warning information check box 252 acts as the position detection/drive control operation unit (11g). The warning information check box 252 is to be checked to make a notification that the tool tip (52a) of the cutting tool 52 attached to the root canal treating hand piece 50 has been detected, by tip position detection, as being close to the root apex (Rt).

The permeability adjustment scroll bar 260 acts as the permeability adjustment operation unit (11c). A knob 261 of the permeability adjustment scroll bar 260 is dragged by the cursor 270 to set the permeability of the converted horizontal cross-sectional image (Cs1) that is to be displayed in the occlusal surface direction image display area 210. In the permeability adjustment scroll bar 260, the knob 261 represents 50% to provide a semi-permeable state in a default setting.

The calibration specification operation unit 280 acts as the calibration operation unit (11i), and is a specification operation unit usable to accept start of calibration on three-dimensional position measurement of the root canal treating hand piece 50.

As described above, the converted horizontal cross-sectional image (Cs1) and the cutting tool tip position image (Ip) are displayed as overlapping the 2D captured image (P), or the cutting tool image (Im) is displayed, on the image overlapping display screen 200 having the above-described structure. While the converted horizontal cross-sectional image (Cs1) and the cutting tool tip position image (Ip) or the cutting tool image (Im) are displayed, a medical care is performed on the root canal (R) of the tooth (T) as the surgical operation target. With reference to the flowcharts in FIG. 6 through FIG. 8, a display method and a surgical operation method used for the medical care are described in more detail.

First, in order to perform a medical care on the root canal (R) of the tooth (T) which is the surgical operation target, the operator acquires 3D information on the tooth (T) and the vicinity thereof including the root canal (R) inside the tooth (T) by use of the X-ray CT image capturing device 40 and stores the 3D information on the 3D information storage unit 31.

The operator captures a 2D captured image (P) of the tooth (T) as the surgical operation target by use of the visible light camera 60 attached to the root canal treating hand piece 50, and displays the 2D captured image (P) in the occlusal surface direction image display area 210 (step (s1)).

In this step, the 2D captured image (P) captured by the visible light camera 60 may be stored on the 2D image information storage unit 32 of the storage device 30 via the control unit 20.

On the 2D captured image (P) displayed in the occlusal surface direction image display area 210, the appoint tooth selection unit 241 acting as the target tooth specification operation unit (11*a*) is operated to specify the target tooth (T) by use of the cursor 270 (step (s2)). Then, the control unit 20 extracts 3D information on the target tooth (T) from the 3D information stored on the 3D information storage unit 31 (step (s3)). The image generation unit 21 generates the converted horizontal cross-sectional image (Cs1) along a plane parallel to the occlusal surface (step (s4)), and displays the converted horizontal cross-sectional image (Cs1) in the occlusal surface direction image display area 210.

When the position of the converted horizontal cross-sectional image (Cs1) displayed in the occlusal surface direction image display area 210 is different from the position of the tooth (T) specified in the 2D captured image (P), the converted horizontal cross-sectional image (Cs1) is dragged to adjust the position thereof. When the size or the orientation of the converted horizontal cross-sectional age (Cs1) is different from that of the tooth (T), the size selection unit 243 or the orientation adjustment selection unit 244 acting as the converted 2D image adjustment operation unit (11*d*) is operated to adjust the size or the orientation of the converted horizontal cross-sectional image (Cs1) so as to be matched to that of the tooth (T) in the 2D captured image (P) (step (s5)).

An example of this operation is described. It is assumed that as shown in FIGS. 10A and 10B, the maximum diameter of the converted horizontal cross-sectional age (Cs1) is longer than that of the tooth (T) in the 2D captured image (P) and extends in a different direction from that of the tooth (T) in the 2D captured image (P). In this case, line (Lp) representing the maximum diameter of the tooth (T) in the 2D captured image (P) is specified (see FIG. 10A), and line (Lc) representing the maximum diameter of the converted horizontal cross-sectional image (Cs1) is specified (see FIG. 10B).

Line Lc of the converted horizontal cross-sectional image (Cs1) is longer than line (Lp) of the tooth (T) in the 2D captured image (P), and line (Lc) extends in a different direction from that of line (Lp) in a counterclockwise direction. Therefore, the converted horizontal cross-sectional image (Cs1) is rotated clockwise such that the angle of line (Lc) of the converted horizontal cross-sectional image (Cs1) matches the angle of line (Lp) of the tooth (T) in the 2D captured image (P). In addition, the converted horizontal cross-sectional image (Cs1) is contracted such that the length of line (Lc) of the converted horizontal cross-sectional image (Cs1) matches the length of line (Lp) of the tooth (T) in the 2D captured image (P). As a result, as shown in FIG. 10C, the converted horizontal cross-sectional image (Cs1) is matched to the tooth (T) in the 2D captured image (P) in both of the orientation and the size, and thus is displayed as overlapping the tooth (T) in the 2D captured image (P) in the occlusal surface direction image display area 210.

The size of the converted horizontal cross-sectional image (Cs1) may be adjusted to the size of the 2D captured image (P) by the following method. An area size of the tooth (T) in the 2D captured image (P) and an area size of the converted horizontal cross-sectional image (Cs1) are found by image analysis, and the size of the converted horizontal cross-sectional image (Cs1) is adjusted such that the two area sizes match each other.

In this manner, the converted horizontal cross-sectional image (Cs1) and the 2D captured image (P) are displayed in the occlusal surface direction image display area 210 in an overlapping manner in correspondence with each other. When there are root canals (R) (step (s6), Yes) in this state, the appoint root canal selection unit 242, acting as the target root canal specification operation unit (11*f*), among the various types of selection operation units 240 is pressed to specify the root canal (R) which is the target of the medical care (step (s7)).

In this manner, one of the root canals (R) is selected as the medical care target in step (s7). When there is only one root canal (R), the converted vertical cross-sectional image (Cs2) along a plane passing the root canal (R) is generated by the image generation unit 21 and displayed in the vertical cross-sectional image display area 220 (step (s8)).

In this state, the converted horizontal cross-sectional image (Cs1) displayed as overlapping the tooth (T) in the 2D captured image (P) is a horizontal cross-sectional image along a plane that is parallel to the occlusal surface and is in the vicinity of the center in the tooth axis direction (up-down direction in FIG. 5) of the tooth (T). Such a plane is represented by the cross-section display line (221*c*) in the vertical cross-sectional image display area 220. When the display position, in the tooth axis direction, at which the converted horizontal cross-sectional image (Cs1) is to be displayed is adjusted by the knob (221*a*), the converted horizontal cross-sectional age (Cs1) along a plane parallel to the occlusal surface at the post-adjustment display position, and the 2D captured image (P), are synthesized by the synthesized image generation and selection unit 24 to generate a synthesized image. The synthesized image is displayed in the occlusal surface direction image display area 210.

Figure 14A:
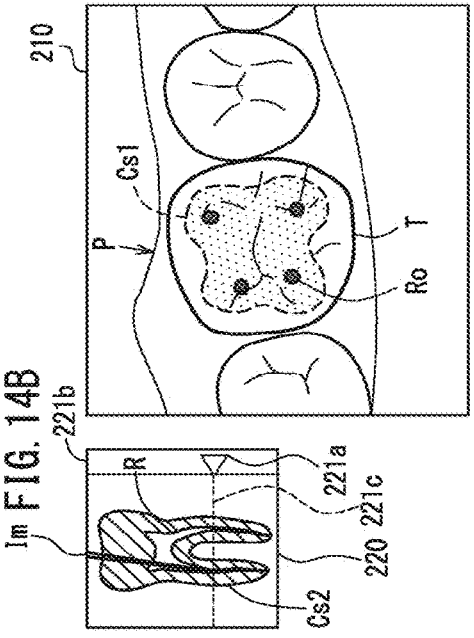
FIGS. 14A, 14B, 14C and 14D show display position adjustment in a tooth axis direction.
Figure 14B:
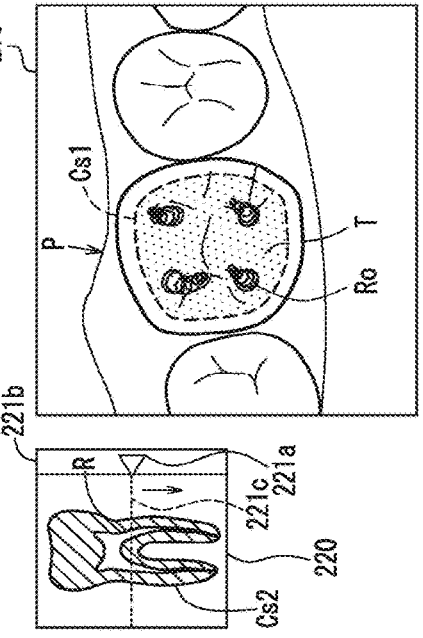
Figure 14C:
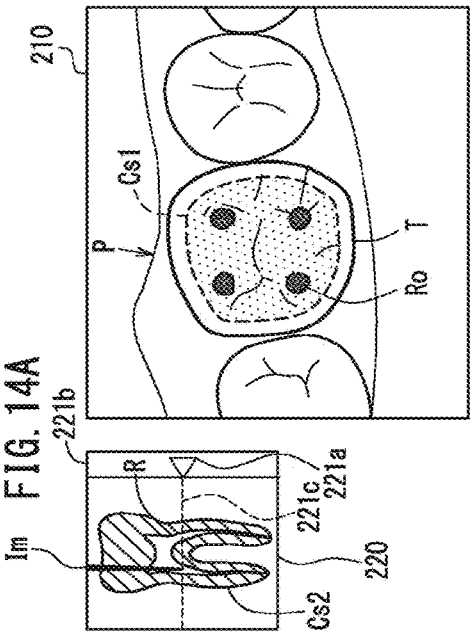

This is described in more detail. FIG. 13 and FIGS. 14A, 14B, 14C and 14D show display position adjustment in the tooth axis direction that is performed in the case where the 2D captured image (P) and the converted horizontal cross-sectional image (Cs1) are displayed in an overlapping manner in the occlusal surface direction image display area 210. When the display position is lowered along the tooth axis toward the root apex (Rt) as shown in FIGS. 14B and 14C from an intermediate position in the default setting (see FIG. 14A) by an operation made on the knob (221*a*), the root canal orifices (Ro) of the root canals (R) displayed in the converted horizontal cross-sectional image (Cs1) approach the root apexes (Rt). Therefore, the positions and the sizes of the root canal orifices (Ro) are changed.

Figure 14D:
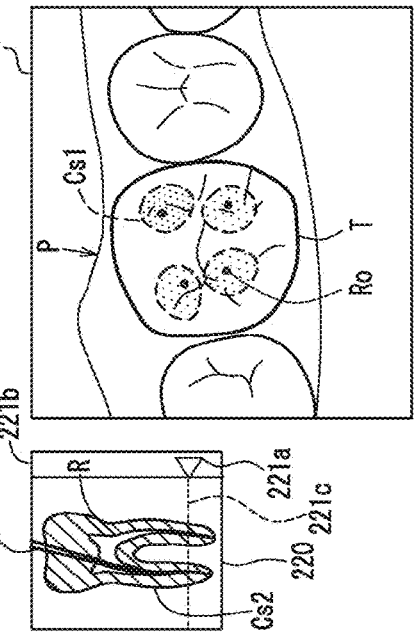

As can be seen, when the knob (221*a*) is operated to continuously change the display position in the tooth axis direction, the root canal orifices (Ro) displayed in the converted horizontal cross-sectional image (Cs1) are changed as shown in FIG. 14D. Therefore, tracks of the root canal orifices (Ro) having substantially the same directivity as that of the root canal extension direction image (Id) is displayed.

In this manner, the converted horizontal cross-sectional image (Cs1) and the 2D captured image (P) that is adjusted so as to correspond to the converted horizontal cross-sectional image (Cs1) are displayed in the occlusal surface direction image display area 210, and also the converted vertical cross-sectional image (Cs2) is displayed in the vertical cross-sectional image display area 220. In this state, the calibration specification operation unit 280 of the image overlapping display screen 200 is pressed to perform the calibration process of initializing a three-dimensional position with respect to the tooth (T) (step (s9)).

This is described in more detail. As shown in FIG. 9, a three-dimensional position measurement marker (56m) is located in the vicinity of the tooth (T) of the patient (M). The tool tip (52a) of the cutting tool 52 of the root canal treating hand piece 50 is in contact with the root canal (R) of the tooth (T). In this state, an image of the three-dimensional position measurement marker 56 of the root canal treating hand piece 50 and an image of the three-dimensional position measurement marker (56m) located in the vicinity of the tooth (T) of the patient (M) are captured by the infrared position detection cameras 81 of the three-dimensional position detection unit 80. The acquired three-dimensional position of the three-dimensional position measurement marker (56m) located in the vicinity of the patient (M) with respect to the three-dimensional position measurement marker 56 of the root canal treating hand piece 50 is set as an initial value.

Namely, the calibration process is performed as follows. The three-dimensional position measurement marker 56 of the root canal treating hand piece 50 that is being used for the surgical operation is detected by the three-dimensional position detection unit 80. Thus, the position of the tool tip (52a) of the cutting tool 52 of the root canal treating hand piece 50 with respect to the tooth (T) is found. As a result, the cutting tool tip position image (Ip) showing the position of the tool tip (52a) of the cutting tool 52, or the cutting tool image (Im), which is an image of the cutting tool 52, are displayed at appropriate positions in the occlusal surface direction image display area 210 or the vertical cross-sectional image display area 220 as overlapping the respective converted cross-sectional image (Cs).

Referring to FIG. 13, it is assumed that "ON" is selected by the ON/OFF switching selection unit 231 of the root canal extension direction image operation unit 230 and thus the root canal extension direction image (Id) is to be displayed as overlapping the 2D captured image (P) or the converted horizontal cross-sectional age (Cs1) in the occlusal surface direction image display area 210 of the image overlapping display screen 200 or as overlapping the converted vertical cross-sectional image (Cs2) in the vertical cross-sectional image display area 220 (step (s10): Yes). In this case, the root canal extension direction image (Id) is generated by the root canal extension direction setting processing unit 22 acting as the root canal extension direction image operation unit (11b) and displayed in an overlapping manner (step (s11)).

This is described in more detail. In the root canal extension direction image operation unit 230, "ON" is selected by the ON/OFF switching selection unit 231, and the appoint point specification unit 232 is pressed to specify multiple arbitrary points on the root canal (R) in the converted vertical cross-sectional image (Cs2) in the vertical cross-sectional image display area 220. When this occurs, the root canal extension direction setting processing unit 22 generates the root canal extension direction image (Id) passing the specified arbitrary points. The root canal extension direction setting processing unit 22 displays the root canal extension direction image (Id) as overlapping the converted horizontal cross-sectional image (Cs1) and the 2D captured image (P) in the occlusal surface direction image display area 210 and also as overlapping the converted vertical cross-sectional image (Cs2) in the vertical cross-sectional image display area 220. The root canal extension direction image (Id) is displayed in an orientation corresponding to the respective area and is displayed together with the cutting tool tip position image (Ip) and the cutting tool image (Im) (step (s11)).

The root canal extension direction image (Id) is a straight line or a curved line drawn based on multiple arbitrary points, for example, two points or three points, specified on the root canal (R). The root canal extension direction image (Id) is displayed as shown in, for example, the occlusal surface direction image display area 210 or the vertical cross-sectional image display area 220. The operator can grasp in which direction the root canal (R) extends using the root canal extension direction image (Id) as a guide and thus can expand the root canal.

Regardless of whether the root canal extension direction image (Id) is displayed (step (s10): Yes) or not (step (s10): No), when the permeability adjustment scroll bar 260 is operated (step (s12): Yes), a synthesized image of the converted horizontal cross-sectional image (Cs1) having permeability adjusted and the 2D captured image (P) is generated by the synthesized image generation and selection unit 24 and displayed in the occlusal surface direction image display area 210 (step (s13)). The permeability adjustment scroll bar 260 acts as the permeability adjustment operation unit 11c for the 2D captured image P and the converted horizontal cross-sectional image (Cs1) displayed in an overlapping manner in the occlusal surface direction image display area 210 of the image overlapping screen 20.

This is described in more detail. FIGS. 11A, 11B and 11C show permeability adjustment performed in the case where the 2D captured image (P) and the converted horizontal cross-sectional image (Cs1) are displayed in an overlapping manner in the occlusal surface direction image display area 210. As shown in FIGS. 11A, 11B and 11C, when the permeability is 50% as in a default setting, the converted horizontal cross-sectional image (Cs1) is permeable and thus the tooth (T) in the 2D captured image (P) is visually recognized (see FIG. 11A).

In this state, the root canal orifices (Ro) of the converted horizontal cross-sectional age (Cs1) are visually recognized on the tooth (T) in the 2D captured image (P). When, for example, the knob 261 is made close to 0%, as shown in FIG. 11B, the converted horizontal cross-sectional image (Cs1) and the root canal orifices (Ro) are difficult to be visually recognized. By contrast, when the knob 261 is made close to 100%, as shown in FIG. 11C, the converted horizontal cross-sectional image (Cs1) is not permeable and thus the tooth (T) in the 2D captured image (P) is difficult to be visually recognized. Therefore, at least one of the converted horizontal cross-sectional image (Cs1) and the 2D captured image (P) may be made permeable to an appropriate degree.

As can be seen, the knob 261 of the permeability adjustment scroll bar 260 may be slid by the cursor 270 to display the converted horizontal cross-sectional image (Cs1) at an arbitrary permeability. The permeability may be adjusted in accordance with, for example, the color of the tooth (T) in the 2D captured image (P) or the brightness of the captured image (P) such that the visibility of the root canal orifices (Ro) in the converted horizontal cross-sectional image (Cs1) is improved. Alternatively, the permeability of the 2D captured image (P) may be adjusted with respect to the converted horizontal cross-sectional image (Cs1) by use of the permeability adjustment scroll bar 260.

The treatment is performed as follows on the root canal (R) specified in step (s7) while the image overlapping display screen 200 is displayed on the monitor 15. First, while the root canal orifice (Ro) is checked in the converted horizontal cross-sectional age (Cs1) which is displayed as overlapping the tooth (T) in the 2D captured image (P) in the occlusal surface direction image display area 210 of the image overlapping display screen 200, the tooth (T) is cut from the side of the tooth crown by the root canal treating hand piece 50 to expose the root canal orifice (Re).

FIGS. 12A and 12B show overlapping display. The photos used in FIGS. 12A and 12B are of the root canal orifices (Ro) exposed by cutting the tectorial part of the tooth (T) by the conventional art. As shown in FIGS. 12A and 12B, in the state where the root canal orifices (Ro) are exposed, the 2D captured image (P) and the converted horizontal cross-sectional image (Cs1) are displayed in the occlusal surface direction image display area 210. FIG. 12A shows that the converted horizontal cross-sectional image (Cs1) showing the root canal orifices (Ro) is displayed as overlapping the tooth (T) in the 2D captured image (P). FIG. 12B shows that the root canal extension direction image (Id) is displayed as overlapping the converted horizontal cross-sectional image (Cs1) and the tooth (T) in the 2D captured image (P). As shown in FIG. 12B, the root canal orifices (Ro) may be numbered so that the root canal orifice (Ro) as the surgical operation target is easily selected from the root canal orifices (Ro). According to an embodiment of the present invention, the tectorial part does not need to be completely removed as is shown in FIGS. 12A and 12B, and the part to be removed is minimized with the healthy area being left as much as possible.

The root canal treatment is performed as follows. The cutting tool 52 is inserted from the root canal orifice (Ro) along a route represented by the root canal extension direction image (Id) to remove a dental pulp. Since bacteria may be even in the dentine of the root canal wall, the root canal wall is removed (expanded cutting) and the inside of the root canal (R) is sterilized. Then, the root canal (R) is filled with natural rubber called Gutta Percha, and the tooth (T) is crowned. Thus, the root canal treatment is finished.

When the three-dimensional position detection unit 80 that detects the three-dimensional position of the head and/or the tooth (T) of the patient (M) detects that the head of the patient (M) has moved (step (s14): Yes) during such a root canal treatment, the position of the cutting tool image (Im) is adjusted with respect to the tooth (T) displayed in the occlusal surface direction image display area 210 or the vertical cross-sectional image display area 220, and the adjusted cutting tool image (Im) is displayed (step (s15)).

In such a root canal treatment, the tip position sensing selection unit 245 of the image overlapping display screen 200 is operated (step (s16): Yes), and the cutting tool 52 is inserted from the root canal orifice (Ro) to perform expanded cutting. At this point, as shown in FIG. 14A through 14C, the cutting tool image (Im) in accordance with the position of the tool tip (52a) of the cutting tool 52 detected by the three-dimensional position detection unit 80 and the position detection processing unit 23 is kept displayed in real time as overlapping the converted cross-sectional image (Cs) in each of the occlusal surface direction image display area 210 and the vertical cross-sectional image display area 220.

Owing to this, the position of the tip tool (52a) with respect to the converted horizontal cross-sectional image (Cs1) or the converted vertical cross-sectional image (Cs2) is kept updated in real time so as to correspond to the progress of the surgical operation of expanding the root canal (Ro). This avoids the tip tool (52a) from coming off from the root canal (R) or piercing the root apex (Rt).

In the example shown in FIGS. 14A, 14B, 14C and 14D, the cutting tool image (Im) showing a part of, or the entirety of, the cutting tool 52 is displayed. The present invention is not limited to this. Alternatively, the cutting tool tip position image (Ip) showing the position of the tool tip (52a) of the cutting tool 52 may be displayed in an overlapping manner.

The tool tip (52a) of the cutting tool 52 is to be displayed in an overlapping manner. However, the position of the tool tip (52a) of the cutting tool 52 is not accurately grasped even though the position of the root canal treating hand piece 50 is detected. A reason for this is that the root canal (R) is generally curved in an area from the root canal orifice (Ro) to the root apex (Rt).

Therefore, position information based on root canal length information measured by the root canal length measurement unit 70 is applied for the position of the tool tip (52a) of the cutting tool 52 (step (s18)). The root canal length information shows the length of the root canal (R) up to the root apex (Rt).

The concept of "application of the position information based on the information on the root canal length measured by the root canal length measurement unit 70" encompasses switching three-dimensional position information acquired by the three-dimensional position detection unit 80 and the position detection processing unit 23 into the position information based on the root canal length information, and defining the position of the tool tip (52a) based on the three-dimensional position information acquired by the three-dimensional position detection unit 80 and the position detection processing unit 23 and also based on the position information based on the root canal length information acquired by the root canal length measurement unit 70. The switching of the position information may be performed at an optimal position in accordance with the degree of curving of the respective root canal (R) by use of a position adjustment unit that is separately provided.

The application of the position information based on the measurement result acquired by the root canal length measurement unit 70 allows the operator to perform the surgical operation while accurately grasping the position of the tool tip (52a) of the cutting tool 52 with respect to the root apex (Rt) in an area relatively close to the root apex (Rt), which is most important for the root canal treatment.

It is now assumed that the tip diversion detection unit 26 detects that the detected tip position of the root canal treating hand piece 50 is close to the root apex (Rt) (step (s19): Yes), or that the tip position of the root canal treating hand piece 50 is not close to the root apex (Rt) but is deviated from the route of the root canal (R) specified by the appoint root canal selection unit 242 (step (s20): Yes), based on the root canal length measurement information acquired by the root canal length measurement unit 70. When the warning information check box 254 is checked in this state (step (s21): Yes), the notification unit 16 makes a notification (step (s22)).

When the drive control check box 251 is checked (step (s23): Yes), the surgical operation tool drive control unit 25 controls the root canal treating hand piece 50 to stop, to advance in a reverse direction, or to be driven at a lower force (step (s24)).

Even when the tip position of the root canal treating hand piece 50 is not detected as being close to the root apex (Rt) (step (s19): No), the root canal treatment needs to be performed with care because the cutting tool 52 performs cutting along the curved root canal (R). When the drive control check box 251 is checked (step (s23)): Yes) and the driving load detection unit 27 detects that the driving load on the root canal treating hand piece 50 exceeds a prescribed load, the surgical operation tool drive control unit 25 controls the root canal treating hand piece 50 to stop, to advance in a reverse direction, or to be driven at a lower force (step (s23)).

The above-described steps are repeated until the root canal treatment is finished (repeated as long as the determination result in step (s25) is No).

In this manner, the medical care system 1 includes the root canal treating hand piece 50 having, attached thereto, the visible light camera 60 that captures the 2D captured image (P) of the tooth (T) as the target of interest, the three-dimensional position detection unit 80 that detects the three-dimensional position of the root canal treating hand piece 50, the monitor 15 that displays the 2D captured image (P), and the image generation unit 21 that displays three images, namely, the converted horizontal cross-sectional image (Cs1) based on the 3D information that includes information on the root canal (R) inside the tooth (T), the 2D captured image (P) captured by the visible light camera 60, and the cutting tool tip position image (Ip) or the cutting tool image (Im), on the monitor 15 in an overlapping manner with the positions thereof being in correspondence with one another. Therefore, the root canal (R) inside the tooth (T) is clearly shown against the 2D captured image (P) captured by the visible light camera 60 displayed on the monitor 15.

This is described in more detail. The three-dimensional position of the root canal treating hand piece 50 having, attached thereto, the visible light camera 60 that captures the 2D captured image (P) of the tooth (T) as the target of interest is detected by the three-dimensional position detection unit 80. Therefore, the image generation unit 21 displays three images, namely, the converted horizontal cross-sectional image (Cs1) generated based on the 3D information that includes information on the root canal (R) inside the tooth (T), the 2D captured image (P) captured by the visible light camera 60, and the cutting tool tip position image (Ip) or the cutting tool image (Im), on the monitor 15 in an overlapping manner with the positions thereof being in accurate correspondence with one another. Therefore, the root canal (R) inside the tooth (T) is clearly shown against the 2D captured image (P) captured by the visible light camera 60 displayed on the monitor 15. Thus, the root canal treatment is performed more precisely and more accurately.

The permeability adjustment scroll bar 260 adjusts the permeability of at least one of the converted horizontal cross-sectional image (Cs1) and the 2D captured image (P) displayed in an overlapping manner in the occlusal surface direction image display area 210. The permeability adjustment scroll bar 260, for example, makes the 2D captured image (P) half-permeable to clearly display the root canal (R) shown in the converted horizontal cross-sectional image (Cs1). By contrast, the permeability adjustment scroll bar 260 may make the converted horizontal cross-sectional image (Cs1) half-permeable to clearly display the 2D captured image (P). In this manner, one of the converted horizontal cross-sectional image (Cs1) and the 2D captured image (P) is displayed clearly against the other, so that the root canal treatment is performed more precisely and more accurately.

The 2D captured image (P) captured in the tooth axis direction of the tooth (T) and the converted horizontal cross-sectional image (Cs1) along a plane that passes the root canal orifices (R) and is perpendicular to the tooth axis direction are displayed in an overlapping manner in the occlusal surface direction image display area 210. Therefore, the converted horizontal cross-sectional image (Cs1) which shows the position and the size of each root canal orifice (Ro) is displayed as overlapping, and in correspondence with, the 2D captured image (P). The 2D captured image (P) is an image in the occlusal surface direction, namely, is an image as seen in the tooth axis direction, in which the line of sight of the operator is directed most often during the root canal treatment. As a result, the position and the size of each root canal orifice (Ro) are clearly shown in the 2D captured image (P). Thus, the root canal treatment is performed more precisely and more accurately.

The root canal treating hand piece 50 includes the root canal length measurement unit 70 that detects the position of the tool tip (52*a*) of the cutting tool 52 attached to the root canal treating hand piece 50, with respect to the root apex (Rt) of the root canal (R). The converted horizontal cross-sectional image (Cs1), which shows a site of the root canal (R) at which the tool tip (52*a*) detected by the root canal length measurement unit 70 is located, is displayed by the image generation unit 21 as overlapping the 2D captured image (P) and the cutting tool tip position image (Ip) or the cutting tool image (Im). Therefore, the tool tip (52*a*), which acts on the site as a target of the surgical operation most directly among parts of the cutting tool 52, is be detected by the root canal length measurement unit 70.

The converted horizontal cross-sectional image (Cs1), which shows a site of the root canal (R) at which the detected tool tip (52*a*) is detected, is displayed on the monitor 15 in an overlapping manner. Therefore, in the state where the tool tip (52*a*) of the cutting tool 52 is displayed on the monitor 15, the operator performing the surgical operation while checking the monitor 15 can accurately grasp the position of the tool tip (52*a*) and check, for example, the position of the root canal (R) with respect to the tool top (52*a*) in the converted horizontal cross-sectional image (Cs1). Thus, the root canal treatment is performed more certainly and more safely.

The converted vertical cross-sectional image (Cs2), which is an image in the tooth axis direction showing a site of the root canal (R) at which the tool tip (52*a*) is located, is displayed in addition to the converted horizontal cross-sectional image (Cs1). The converted vertical cross-sectional image (Cs2) is displayed in the vertical cross-sectional image display area 220 together with the cutting tool tip position image (Ip) or the cutting tool image (Im). Therefore, the operator, performing the surgical operation while checking the monitor 15, can keep checking, for example, the position of the tool tip (52*a*) with respect to the root apex (Rt) in the converted horizontal cross-sectional image (Cs1) continuously in real time, and also can keep checking the position of the tool tip (52*a*) detected by the root canal length measurement unit 70 in the converted vertical cross-sectional image (Cs2). Therefore, the position of the tool tip (52*a*) is grasped more accurately, and the root canal treatment is performed more safely.

The vertical cross-sectional image display area 220 shows the scale (221d), so that the distance from the tip position of the root canal treating hand piece 50 to the root apex (Rt) is checked.

The converted horizontal cross-sectional image (Cs1), which shows a site of the root canal (R) at which the tool tip (52a) is located, is displayed. In addition, the root canal extension direction image (Id), which shows the direction in which the root canal (R) extends toward the root apex (Rt), is displayed by the root canal extension direction image operation unit 230. Therefore, the direction of the root canal (R) extends inside the tooth (T) as the target of interest is clearly shown against the 2D captured image (P).

This is described in more detail. The root canal extension direction image (Id), which shows the root canal extension direction, namely, the direction in which the root canal (R) inside the tooth (T) extends toward the outside of the tooth crown, is displayed based on the 3D information as overlapping the 2D captured image (P). Owing to this, on the 2D capture image (P), which shows only the surface, the shape of the root canal (R) inside the tooth (T) is clearly shown. The root canal extension direction image (Id) acts as, for example, a guide that guides the direction in which the cutting tool 52 is to be inserted into the root canal (R). Thus, the root canal treatment is performed more accurately and more safely.

It is now assumed that the root canal length measurement unit 70 detects that the tool tip (52a) has reached a predetermined position in the root canal (R). In this case, when, for example, the tool tip (52a) is at a position several millimeters before the root apex (Rt), a notification is made in the form of voice, buzzer, melody, vibration, or lighting or blinking of an LED or the like. Alternatively, in such a case, the root canal treating hand piece 50 is controlled, for example, to stop, to advance in a reverse direction, or to be driven at a lower force. Therefore, the operator can perform the surgical operation carefully and certainly while recognizing that the tool tip (52a) is approaching the root apex (Rt) before the tool tip (52a) reaches the root apex (Rt).

The three-dimensional position detection unit 80 detects the three-dimensional position of the root canal treating hand piece 50 and also the three-dimensional position of an area in the vicinity of the tooth (T) of the patient (M) as the surgical operation target. Therefore, even when the head and/or the tooth (T) of the patient (M) moves during the treatment, the root canal treating hand piece 50 and the cutting tool 52 are displayed accurately on the monitor 15.

The visible light camera in an embodiment of the present invention corresponds to the visible light camera 60 or the microscope (not shown) in the above-described embodiment; and in the same manner, the position detection unit and the first position detection unit corresponds to the three-dimensional position detection unit 80;

the display unit corresponds to the monitor 15;

the three-dimensional information on the tooth corresponds to the 3D information;

the cross-sectional image corresponds to the converted horizontal cross-sectional image (Cs1);

the image processing unit corresponds to the image generation unit 21;

the root canal treatment device corresponds to the medical care system 1;

the visible light image corresponds to the 2D captured image (P);

the cross-sectional image of a horizontal cross-section and a vertical cross-section taken along the tooth axis direction corresponds to the converted horizontal cross-sectional image (Cs1);

the cross-sectional image of a vertical cross-section corresponds to the converted vertical cross-sectional image (Cs2);

the root canal extension direction image corresponds to the root canal extension direction image (Id);

the predetermined operation control unit corresponds to the control unit 20;

the second position detection unit corresponds to the three-dimensional position detection unit 80 in the case of detecting the three-dimensional position measurement marker (56m); and the torque detection unit corresponds to the driving load detection unit 27.

However, the present invention is not limited to the above-described embodiment, and may be carried out in any of various other embodiments.

In the above description, for the root canal treatment, the cutting tool image (Im) of the cutting tool 52 is displayed as overlapping the 2D captured image (P) in the occlusal surface direction image display area 210 of the image overlapping display screen 200 and is also displayed in the vertical cross-sectional image display area 220 of the image overlapping display screen 200. Referring to FIG. 15, as represented by the dashed line, a trace image (Ir) showing a trace of the cutting tool 52 may be displayed in an overlapping manner, in addition to the cutting tool image (Im) displayed as overlapping the 2D captured image (P).

Figure 16:
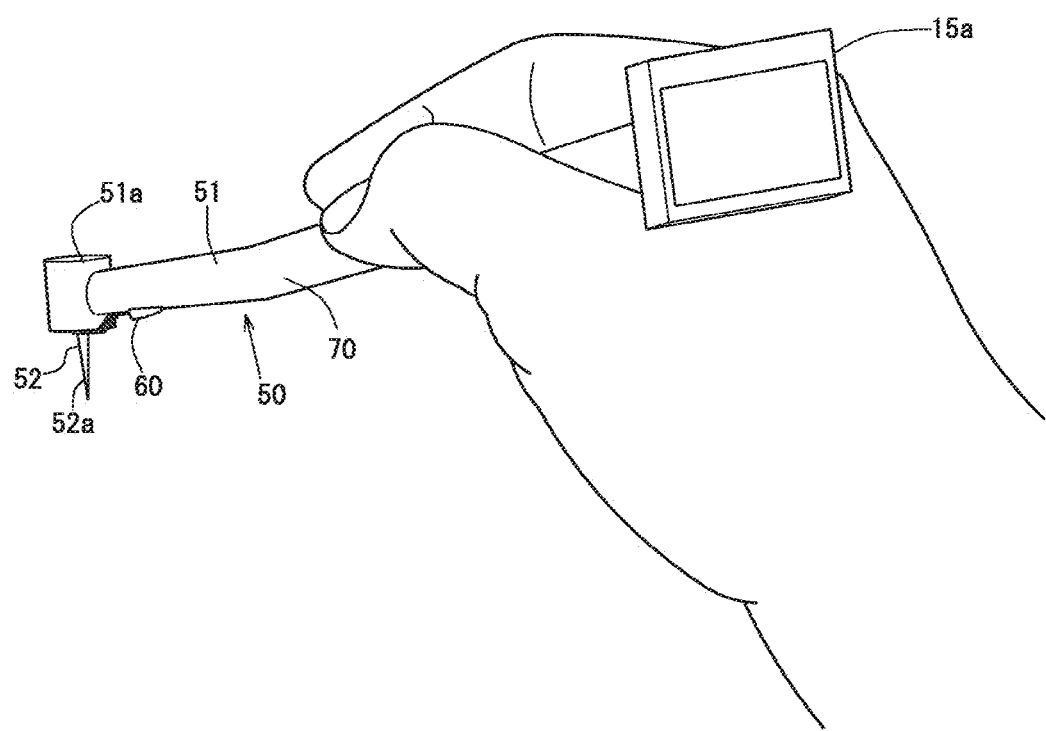
FIG. 16 is a schematic isometric view of a root canal treating hand piece according to another embodiment of the present invention as seen from a rear side thereof.

In the above description, the image overlapping display screen 200 is displayed on the monitor 15. Alternatively, as shown in FIG. 16, a monitor (15a) may be provided at a rear end of the root canal treating hand piece 50, and a screen similar to the image overlapping display screen 200 may be displayed on the monitor (15a). In this case, the line of sight of the operator moves less. In addition, the direction in which the root canal treating hand piece 50 is moved is substantially the same as the direction of the line of sight. This prevents difficulty in the surgical operation from being caused by the direction in which the root canal treating hand piece 50 is moved being different from the direction of the line of sight.

In the image overlapping display screen 200 described above, the converted horizontal cross-sectional image (Cs1) may be displayed in an area different from the 2D captured image (P) displayed in the occlusal surface direction image display area 210, so that the converted horizontal cross-sectional image (Cs1) and the 2D captured image (P) are displayed side by side.

In the above description, the converted vertical cross-sectional image (Cs2), which is a cross-sectional image of the tooth (T), is displayed in the vertical cross-sectional image display area 220. Alternatively, a side view of the tooth (T) may be displayed. Still alternatively, only the 2D captured image (P) may be displayed, namely, the converted horizontal cross-sectional image (Cs1) may not be displayed, in the occlusal surface direction image display area 210, and the converted vertical cross-sectional image (Cs2) may be displayed in the vertical cross-sectional mage display area 220.

A visible light two-dimensional image is desirably captured by a visible light camera integrally built in, or attached to, the root canal treating hand piece 50. Alternatively, the visible light two-dimensional image may be captured by an intraoral camera, a microscope, an endoscope or an optical camera separately provided from the root canal treating hand piece 50.

In the above description, the size or the orientation of the converted horizontal cross-sectional image (Cs1) is adjusted so as to be suitable to the 2D captured image (P). Alternatively, the size or the orientation of the 2D captured image (P) may be adjusted so as to be suitable to the converted horizontal cross-sectional age (Cs1). Still alternatively, both of the converted horizontal cross-sectional image (Cs1) and the 2D captured image (P) may be adjusted to be suitable to each other.

In the examples shown in FIG. 5, FIG. 13, FIGS. 14A, 14B, 14C and 14D and FIG. 15, the horizontal cross-sectional image taken along a plane perpendicular to the tooth axis is used. The present invention is not limited to this. An X-ray image of the tooth (T) taken along a plane oblique to the tooth axis may be used as far as the age is of a cross-section of the tooth (T). In this case, use of an image along a plane having an angle of ±30 degrees with respect to the tooth axis is encompassed in an embodiment of the present invention.

In the converted horizontal cross-sectional image (Cs1), the root canal orifices (Ro) may be colored, and only the colored root canal orifices (Ro) may be displayed as overlapping the 2D captured image (P). Alternatively, in the converted horizontal cross-sectional image (Cs1), the outline of the tooth (T) or the root canal orifices (Ro) may be emphasized, and the tooth (T) or the root canal orifices (Ro) in such a state may be displayed as overlapping the 2D captured image (P).

The visible light camera 60 may be, for example, a three-dimensional optical camera such as a stereo camera or the like, or an intraoral camera, provided separately from the root canal treating hand piece 50, and a three-dimensional visible light image may be used as the visible light image. The cutting tool 52 may be a file, a reamer, or an illumination chip that directs laser light. The visible light camera provided separately from the root canal treating hand piece 50 may be oriented in the same direction as the root canal treating hand piece 50.

In the above description, an image of the three-dimensional position measurement marker 56 is captured by the three-dimensional position detection unit 80 including the pair of infrared position detection cameras 81 to detect the three-dimensional position of the root canal treating hand piece 50. Alternatively, the three-dimensional position may be detected by a combination of measurement of the posture of the root canal treating hand piece 50 performed by the posture detection unit 54 built in the root canal treating hand piece 50 and measurement of the two-dimensional position of the root canal treating hand piece 50 performed by use of two or more points on the root canal treating hand piece 50.

In the above description, the permeability adjustment scroll bar 260 makes permeable one of the 2D captured image (P) and the converted horizontal cross-sectional image (Cs1) displayed in the occlusal surface direction image display area 210 in an overlapping manner. Such an image may be made colorless and permeable or colored and permeable. Alternatively, the permeability adjustment scroll bar 260 may make permeable both of the 2D captured image (P) and the converted horizontal cross-sectional image (Cs1).

The image showing the tool tip (52*a*) of the cutting tool 52 may be provided in the form of a point or blinking showing the position of the tool tip 52 of the cutting tool 52. Alternatively, a part of, or the entirety of, the cutting tool 52 may be displayed.

In the above description, the horizontal cross-sectional image and the vertical cross-sectional image of the tooth (T) are each displayed as the X-ray cross-sectional image. Alternatively, the X-ray cross-sectional age may be an image of a sagittal plane, a coronal plane or a cross-sectional plane.

The visible light camera is attached to the root canal treating hand piece 50. This concept encompasses that the visible light camera is attached to an outer circumference of the root canal treating hand piece 50 by an attaching tool, and that the visible light camera is built in the root canal treating hand piece 50.

In the fields of dental care, a precise root canal treatment on a tooth may be performed by capturing and observing an image of the tooth by use of an optical camera referred to as an "intraoral camera" or a microscope.

However, a visible light image captured by the optical camera or the microscope is an image of a surface of the tooth in an occlusal surface direction, and a root canal orifice or the like inside the tooth is not checked by the visible light image.

In an attempt to solve such a problem, CT image capturing is performed. According to the CT image capturing, a tooth as a target of interest is irradiated with an X-ray to collect projection data, and the acquired projection data is re-constructed on a computer to generate a computer tomography image (volume rendering image, etc.).

The CT image capturing is performed as follows. A subject is located between an X-ray generator and an X-ray detector. While the X-ray generator and the X-ray detector are revolved around the subject, a cone-like X-ray is directed toward the subject from the X-ray generator. The X-ray detection results are collected by the X-ray detector, and three-dimensional data is re-constructed based on the collected X-ray detection results. A device for performing such CT image capturing is described in, for example, Japanese Laid-Open Patent Publication No. 2006-305203.

An X-ray CT image capturing device described in Japanese Laid-Open Patent Publication No. 2006-305203 displays a volume rendering image in addition to a cross-sectional image taken along each of X, Y and Z directions. An X cursor, a Y cursor and a Z cursor are operated to display cross-sections corresponding to the respective cursors.

In such CT image capturing, information on the tooth acquired by the X-ray transmitted through the tooth includes information on the root canal inside the tooth. Therefore, the position or the size of the root canal orifice or the like, which cannot be visually recognized from the surface, can be shown.

However, an operator needs to perform a treatment while checking the visible light image captured by the optical camera or the microscope. Therefore, the operator needs to imagine synthesizing the CT image and the visible light image captured by the optical camera or the microscope three-dimensionally while performing the treatment. For example, it is difficult to accurately grasp the position of the root canal orifice inside the tooth while checking a visible light image of the surface of the tooth captured by the optical camera or the microscope. There is a risk that the root canal is excessively cut even into the healthy area other than the root canal orifice.

Japanese PCT National-Phase Laid-Open Patent Publication No. 2013-519479 describes a three-dimensional imaging device that displays points or lines showing the shape of a root canal on a cross-sectional image of a tooth acquired by an X-ray CT image capturing device.

The three-dimensional imaging device described in Japanese PCT National-Phase Laid-Open Patent Publication No. 2013-519479 merely displays the points and lines showing the shape of the root canal on the cross-sectional image of the tooth acquired by the X-ray CT image capturing device. Japanese PCT National-Phase Laid-Open Patent Publication No. 2013-519479 does not disclose, for example, a visible light image and a cross-sectional image of the tooth being displayed in an overlapping manner.

Japanese Laid-Open Patent Publication No. 2011-30637 describes the following technology for treating a root canal. A detection result acquired by a root canal length measurement unit and a three-dimensional X-ray image captured by an X-ray image capturing device are used, and a detection signal from the root canal length measurement unit is displayed as overlapping the three-dimensional X-ray image to show the distance to the root apex on the three-dimensional X-ray image.

Even with the image display technology described in Japanese Laid-Open Patent Publication No. 2011-30637, a cutting tool cannot be guided to a target root canal unless a large area of the tectorial part is removed so that the root canal is visually recognizable as in the conventional art. In addition, the precision of the root canal length measurement unit is low in the root canal orifice and the vicinity thereof that is far from the root apex. Therefore, a healthy area also needs to be cut. Furthermore, a cutting tool attached to the root canal treating hand piece cannot be guided to the root canal orifice accurately.

A root canal treating device according to an embodiment of the present invention clearly displays, against an image of a tooth, a root canal inside the tooth at a position of a tip of a cutting tool. The root canal treating device realizes the clear display by displaying three images, namely, an image corresponding to at least a tip position of the cutting tool attached to a root canal treating hand piece which is being used for a root canal treatment, an X-ray cross-sectional image of the tooth that is captured by X-ray CT image capturing beforehand and corresponds to the tip position of the cutting tool, and a visible light image captured by a visible light camera. The three images are displayed on a display unit in positional correspondence with one another, based on information on the position of the root canal treating hand piece detected by the position detection unit.

A root canal treating device according to an embodiment of the present invention includes a root canal treating hand piece having, attached thereto, a visible light camera that captures a visible light image of a tooth as a target of interest; a position detection unit that detects a position of the root canal treating hand piece; a display unit that displays the visible light image; and an image processing unit that displays three images of an image corresponding to at least a tip position of a cutting tool attached to the root canal treating hand piece, an X-ray cross-sectional image of the tooth captured by X-ray CT image capturing beforehand, and the visible light image captured by the visible light camera, the three images being displayed on the display unit in an overlapping manner in positional correspondence with one another, based on information on the position of the root canal treating hand piece detected by the position detection unit.

The visible light camera that captures a visible light image encompasses an optical camera that captures a two-dimensional image of a surface of the tooth, and a three-dimensional optical camera that captures three-dimensional image of the surface of the tooth, for example, a stereo camera or the like.

The cutting tool may be a file, a reamer, or an illumination chip that directs laser light.

The position detection unit may be, for example, a non-contact three-dimensional position detection device or a root canal length measurement device. The non-contact three-dimensional position detection device may be, for example, a gyrosensor built in the root canal treating hand piece; a three-dimensional position measurement device that uses an infrared reflective member including multiple small balls attached to the root canal treating hand piece and infrared rays usable to measure a three-dimensional position of the infrared reflective member; or a three-dimensional position measurement device that detects a three-dimensional position by use of a magnetic field emitted from a magnetic field generation source attached to the root canal treating hand piece. Whereas the non-contact position detection device detects a spatial three-dimensional position, the root canal length measurement device measures a distance from the tip position of the cutting tool to a root apex of the tooth as a target of interest.

The detection of information on the position of the root canal treating hand piece performed by the position detection unit encompasses, for example, the following types of non-contact three-dimensional position detection: measurement of three-dimensional positions of at least two points on the root canal treating hand piece performed by a three-dimensional position measurement device using infrared rays; a combination of measurement of a three-dimensional position of at least one point on the root canal treating hand piece and measurement performed by a gyrosensor built in the root canal treating hand piece; and a combination of measurement of two-dimensional positions of at least two points on the root canal treating hand piece and measurement performed by the gyrosensor.

The image corresponding to at least the tip position of the cutting tool may be a dotted image corresponding to the tip position of the cutting tool, or an image showing a part of, or the entirety of, the cutting tool. The dotted image may be blinking so as to be easily recognizable.

The visible light image and the X-ray cross-sectional image displayed together with the image corresponding to at least the tip position of the cutting tool encompasses a still image and a moving image.

Specifically, the image captured by the visible light camera may be a still image or a moving image. In the case where the image captured by the visible light camera is a moving image, the X-ray cross-sectional image to be displayed as overlapping the visible light image is subjected to a moving image process. In the moving image process, the outline of the tooth or the position of the root canal in the visible light image are recognized, so that the moving X-ray cross-sectional image follows the change in the position or the orientation of the moving visible light image.

As described above, according to an embodiment of the present invention, three images, namely, an image corresponding to at least a tip position of a cutting tool attached to the root canal treating hand piece, an X-ray cross-sectional image of the tooth captured by X-ray CT image capturing beforehand, and the visible light image captured by the visible light camera are displayed on a display unit in an overlapping manner in positional correspondence with one another. Such display encompasses matching the image corresponding to at least the tip position, the X-ray cross-sectional image, and the visible light image in terms of the position, orientation, external shape, size or the like.

According to an embodiment of the present invention, the root canal inside the tooth is clearly shown against the visible light image captured by the visible light camera that is displayed on the display unit.

This is described in more detail. The position detection unit detects the position of the root canal treating hand piece having, attached thereto, the visible light camera that captures a visible light image of the tooth as a target of interest. Thus, the image processing unit displays three images, namely, the image corresponding to the tip position of the cutting tool, the X-ray cross-sectional image generated based on information on the position of the tooth including information on the root canal inside the tooth, and the visible light image captured by the visible light camera, on the display unit in accurate positional correspondence with one another. Therefore, the root canal inside the tooth is clearly shown against the visible light image captured by the visible light camera that is displayed on the display unit, and also the tip position of the cutting tool with respect to the root canal is checked. Therefore, the root canal treatment is performed more precisely and more accurately.

In an embodiment according to the present invention, the X-ray cross-sectional image may be an X-ray cross-sectional image of at least one of a horizontal cross-section taken along a plane passing the tip position of the cutting tool and perpendicular to a tooth axis direction, and a vertical cross-section taken along the tooth axis direction.

According to an embodiment of the present invention, it can be checked in real time whether the tip of the cutting tool is off the root canal or whether the tip is piercing the root apex, based on an appropriate X-ray cross-sectional image such as a horizontal cross-sectional mage, a vertical cross-sectional image or the like. Therefore, the surgical operation is advanced accurately.

The image processing unit may display one of, or both of, the X-ray vertical cross-sectional image and the X-ray horizontal cross-sectional image, each of which shows the tip position in the root canal.

In an embodiment according to the present invention, the position detection unit may include at least one of a root canal length measurement unit that detects a position of the cutting tool attached to the root canal treating hand piece with respect to a root apex, and a non-contact three-dimensional position detection unit.

According to an embodiment of the present invention, the three-dimensional position of a site as a target of the surgical operation for the root canal treatment is detected accurately by an appropriate method.

This is described in more detail.

In position detection performed by the root canal length measurement unit, a distance from the tip position of the cutting tool to the root apex, which is important for the root canal treatment, is detected although such a distance is not spatial three-dimensional position measurement information. A surgical operation on an area from the tooth crown to the root canal orifice can be performed by use of a cutting tool that is hard and is not deformed even if an air turbine hand piece or the like is used as the root canal treating hand piece. A spatial position of the root canal treating hand piece is measured by the above-described non-contact three-dimensional position detection unit. Thus, the tip position of the cutting tool is estimated.

However, in an area from the root canal orifice to the root apex, the tip position of the cutting tool cannot be measured even though the spatial position of the root canal treating hand piece can be detected. A reason for this is that the root canal is generally curved in this area. Instead, a distance from the tip position of the cutting tool to the root apex is estimated based on the result of measurement acquired by the root canal length measurement unit.

In this area, a micromotor hand piece or an ultrasonic scaler hand piece for root canal treatment, each of which generally has a low rotation rate, is used. As the cutting tool usable therefor, a reamer or a file compatible to the curved root canal, or a scaler chip which can be curved, may be used.

As described above, as information to be used by the position detection unit, information from the three-dimensional position measurement unit and information from the root canal length measurement unit may be switched at a predetermined site in the root canal. Alternatively, in the case where the root canal is straight, both information may be used.

The surgical operation may be performed based only on the information from the three-dimensional position measurement unit or the information from the root canal length measurement unit.

In an embodiment according to the present invention, the image processing unit may display the X-ray cross-sectional image and the visible light image in an overlapping manner with at least one of the X-ray cross-sectional image and the visible light image being permeable.

The expression "with at least one of the X-ray cross-sectional image and the visible light image being permeable" refers to making at least one of the X-ray cross-sectional image and the visible light image semi-permeable, colored and permeable, or completely permeable. The concept represented by this expression encompasses making one of the X-ray cross-sectional image and the visible light image permeable in order to clearly display the other, and also making both of the images at different degrees of permeability.

According to an embodiment of the present invention, the visible light image, for example, is made semi-permeable to clearly display the root canal shown in the X-ray cross-sectional image. By contrast, the X-ray cross-sectional image is made semi-permeable to clearly display the visible light image. In this manner, one of the X-ray cross-sectional image and the visible light image displayed in an overlapping manner is clearly shown against the other, so that the root canal treatment is performed more precisely and more accurately. In addition, while one of the images is clearly displayed, the other image may be made permeable or non-permeable. In this manner, the treatment can be performed while one of the images that is clearly displayed is mainly checked.

In an embodiment according to the present invention, the display unit may display a root canal extension direction image showing a direction in which the root canal extends toward a root apex.

According to an embodiment of the present invention, the direction of the root canal inside the tooth as the target of interest is clearly displayed on the image of the tooth.

This is described in more detail. The root canal extension direction image shows a root canal extension direction, in which the root canal inside the tooth extends toward the outside of the tooth crown. The root canal extension direction image is displayed as overlapping the visible light age or the cross-sectional image based on the three-dimensional information on the tooth. Owing to this, on the visible light image, which shows only the surface, the shape of the root canal inside the tooth is clearly shown. For example, the root canal extension direction image guides the direction in which the cutting is to be inserted into the root canal. Thus, the root canal treatment is performed more accurately and more safely.

In an embodiment according to the present invention, the root canal treating device further includes an operation control unit that, when the position detection unit detects that the tip position has reached a predetermined position in the root canal, performs one of an operation of stopping driving the root canal treating hand piece, an operation of advancing the root canal treating hand piece in a reverse direction, and an operation of decreasing a force of driving the root canal treating hand piece.

The predetermined position in the root canal may be an arbitrary position in the root canal between the root canal orifice and the root apex, for example, a position that is a predetermined distance away from the root apex.

According to an embodiment of the present invention, when, for example, the tip position of the cutting tool reaches a predetermined position before the root apex, for example, a position several millimeters before the root apex, the root canal treating hand piece is controlled, for example, to stop, to advance in a reverse direction, or to be driven at a lower force, as predetermined. Therefore, the treatment can be performed safely. In addition to the above control being performed, a notification may be made in the form of voice, buzzer, melody, vibration, or lighting or blinking of an LED or the like.

In an embodiment according to the present invention, the display unit may display a trace of movement of the tip position of the cutting tool.

According to an embodiment of the present invention, the operator can perform the surgical operation without, for example, imposing an excessive load on the cutting tool while checking the trace of movement of the tip position.

In an embodiment according to the present invention, in the state where the position detection unit is a first position detection unit, the root canal treating device may further include a second position detection unit that detects a three-dimensional position of a head and/or the tooth of a patient as a target of a surgical operation.

The concept represented by the "second position detection unit that detects a three-dimensional position of a head and/or the tooth of a patient" encompasses a detection unit that detects an absolute three-dimensional position of the root canal treating hand piece and an absolution three-dimensional position of the head or the tooth and calculates a positional relationship between the root canal treating hand piece and the head or the tooth, and a detection unit that detects a three-dimensional position of the head or the tooth with respect to the root canal treating hand piece.

According to an embodiment of the present invention, even when the head and/or the tooth of the patient moves during the treatment, the root canal treating hand piece and the cutting tool are displayed accurately on the display unit.

In an embodiment according to the present invention, the root canal treating device may further include a torque detection unit that detects a torque value applied on the cutting tool. When the torque value detected by the torque detection unit exceeds a predetermined value, the operation control unit may perform one of an operation of stopping driving the root canal treating hand piece, an operation of advancing the root canal treating hand piece in a reverse direction, and an operation of decreasing a force of driving the root canal treating hand piece.

According to an embodiment of the present invention, an inconvenience that, for example, the cutting tool is broken by receiving an excessive load is avoided.

A root canal treating device according to an embodiment of the present invention displays three images, namely, an image corresponding to at least a tip position, which is continuously changed, of a cutting tool attached to a root canal treating hand piece that is being used for a surgical operation, an X-ray cross-sectional image of a tooth that corresponds to the tip position and is captured by X-ray CT image capturing beforehand, and a visible light image captured by a visible light camera, on a display unit in an overlapping manner in positional correspondence with one another, and thus avoids the cutting tool from coming off from the toot canal or piercing the root apex.

Obviously, numerous modifications and variations of the present invention are possible in light of the above teachings. It is therefore to be understood that within the scope of the appended claims, the invention may be practiced otherwise than as specifically described herein.

The invention claimed is:

1. A root canal treatment apparatus, comprising:
   a root canal treating hand piece having a visible light camera configured to capture a visible light image of a tooth as a target of interest; and
   circuitry configured to detect a position of the root canal treating hand piece, and instruct display of three images corresponding to at least a tip position of a cutting tool attached to the root canal treating hand piece, an X-ray cross-sectional image of the tooth captured by X-ray CT image capturing beforehand, and the visible light image captured by the visible light camera such that the three images are displayed on a display in an overlapping manner in positional correspondence with one another, based on information on the position of the root canal treating hand piece detected by the circuitry.

2. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction.

3. The root canal treatment device according to claim 1, wherein the circuitry is configured to detect a position of the cutting tool attached to the root canal treating hand piece with respect to a root apex.

4. The root canal treatment device according to claim 1, wherein the circuitry is further configured to instruct display of the X-ray cross-sectional image and the visible light image in an overlapping manner with at least one of the X-ray cross-sectional image and the visible light image being permeable.

5. The root canal treatment device according to claim 1, wherein the circuitry is further configured to instruct display of a root canal extension direction image showing a direction in which the root canal extends toward a root apex on the display.

6. The root canal treatment device according to claim 1, wherein the circuitry is further configured to, when the tip position has been detected to have reached a predetermined position in the root canal, perform one of an operation of stopping driving the root canal treating hand piece, an operation of advancing the root canal treating hand piece in a reverse direction, and an operation of decreasing a force of driving the root canal treating hand piece.

7. The root canal treatment device according to claim 1, wherein the circuitry is further configured to display a trace of movement of the tip position of the cutting tool.

8. The root canal treating device according to claim 1, wherein the circuitry is further configured to detect a three-dimensional position of a head and/or the tooth of a patient as a target of a surgical operation.

9. The root canal treatment device according to claim 1, wherein the circuitry is further configured to detect a torque value applied on the cutting tool, and when the torque value exceeds a predetermined value, the circuitry is further configured to perform one of an operation of stopping driving the root canal treating hand piece, an operation of advancing the root canal treating hand piece in a reverse direction, and an operation of decreasing a force of driving the root canal treating hand piece.

10. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, and the circuitry is configured to detect a position of the cutting tool attached to the root canal treating hand piece with respect to a root apex.

11. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, the circuitry is configured to detect a position of the cutting tool attached to the root canal treating hand piece with respect to a root apex, and the circuitry is further configured to instruct display of the X-ray cross-sectional image and the visible light image in an overlapping manner with at least one of the X-ray cross-sectional image and the visible light image being permeable.

12. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, the circuitry is configured to detect a position of the cutting tool attached to the root canal treating hand piece with respect to a root apex, the circuitry is further configured to instruct display of the X-ray cross-sectional image and the visible light image in an overlapping manner with at least one of the X-ray cross-sectional image and the visible light image being permeable, and the circuitry is further configured to instruct display of a root canal extension direction image showing a direction in which the root canal extends toward a root apex on the display.

13. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, the circuitry is configured to detect a position of the cutting tool attached to the root canal treating hand piece with respect to a root apex, the circuitry is further configured to instruct display of the X-ray cross-sectional image and the visible light image in an overlapping manner with at least one of the X-ray cross-sectional image and the visible light image being permeable, the circuitry is further configured to instruct display of a root canal extension direction image showing a direction in which the root canal extends toward a root apex on the display, and the circuitry is further configured to, when the tip position has been detected to have reached a predetermined position in the root canal, perform one of an operation of stopping driving the root canal treating hand piece, an operation of advancing the root canal treating hand piece in a reverse direction, and an operation of decreasing a force of driving the root canal treating hand piece.

14. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, the circuitry is configured to detect a position of the cutting tool attached to the root canal treating hand piece with respect to a root apex, the circuitry is further configured to instruct display of the X-ray cross-sectional image and the visible light image in an overlapping manner with at least one of the X-ray cross-sectional image and the visible light image being permeable, the circuitry is further configured to instruct display of a root canal extension direction image showing a direction in which the root canal extends toward a root apex on the display, the circuitry is further configured to, when the tip position has been detected to have reached a predetermined position in the root canal, perform one of an operation of stopping driving the root canal treating hand piece, an operation of advancing the root canal treating hand piece in a reverse direction, and an operation of decreasing a force of driving the root canal treating hand piece, and the circuitry is further configured to display a trace of movement of the tip position of the cutting tool.

15. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, the circuitry is configured to detect a position of the cutting tool attached to the root canal treating hand piece with respect to a root apex, the circuitry is further configured to instruct display of the X-ray cross-sectional image and the visible light image in an overlapping manner with at least one of the X-ray cross-sectional image and the visible light image being permeable, the circuitry is further configured to instruct display of a root canal extension direction image showing a direction in which the root canal extends toward a root apex on the display, the circuitry is further configured to, when the tip position has been detected to have reached a predetermined position in the root canal, perform one of an operation of stopping driving the root canal treating hand piece, an operation of advancing the root canal treating hand piece in a reverse direction, and an operation of decreasing a force of driving the root canal treating hand piece, the circuitry is further configured to display a trace of movement of the tip position of the cutting tool, and the circuitry is further configured to detect a three-dimensional position of at least one of a head and the tooth of a patient as a target of a surgical operation.

16. The root canal treatment device according to claim 1, wherein the X-ray cross-sectional image is an X-ray cross-sectional image of at least one of a horizontal cross-section taken along a plane passing the tip position of the cutting tool and perpendicular to a tooth axis direction, and a vertical cross-section taken along the tooth axis direction, the circuitry is configured to detect a position of the cutting tool attached to the root canal treating hand piece with respect to a root apex, the circuitry is further configured to instruct display of the X-ray cross-sectional image and the visible light image in an overlapping manner with at least one of the X-ray cross-sectional image and the visible light image being permeable, the circuitry is further configured to instruct display of a root canal extension direction image showing a direction in which the root canal extends toward a root apex on the display, the circuitry is further configured to, when the tip position has been detected to have reached a predetermined position in the root canal, perform one of an operation of stopping driving the root canal treating hand piece, an operation of advancing the root canal treating hand piece in a reverse direction, and an operation of decreasing a force of driving the root canal treating hand piece, the circuitry is further configured to display a trace of movement of the tip position of the cutting tool, the circuitry is further configured to detect a three-dimensional position of at least one of a head and the tooth of a patient as a target of a surgical operation, the circuitry is further configured to detect a torque value applied on the cutting tool, and when the detected torque value exceeds a predetermined value, the circuitry is further configured to perform one of an operation of stopping driving the root canal treating hand piece, an operation of advancing the root canal treating hand piece in a reverse direction, and an operation of decreasing a force of driving the root canal treating hand piece.

* * * * *